US012599377B2

(12) United States Patent     (10) Patent No.: US 12,599,377 B2

Kellar et al.     (45) Date of Patent: Apr. 14, 2026

(54) KNEE TENSIONER-BALANCER AND METHOD

(71) Applicant: Little Engine, LLC, Belmont, NC (US)

(72) Inventors: Franz W. Kellar, Gastonia, NC (US); Michael D. Bissette, Belmont, NC (US); Harold L. Crowder, Concord, NC (US)

(73) Assignee: DYNAMIC BALANCER SYSTEMS LLC, Belmont, NC (US)

( * ) Notice: Subject to any disclaimer, the term of this patent is extended or adjusted under 35 U.S.C. 154(b) by 0 days.

(21) Appl. No.: 18/307,403

(22) Filed: Apr. 26, 2023

(65) Prior Publication Data

US 2023/0389913 A1     Dec. 7, 2023

Related U.S. Application Data

(63) Continuation of application No. 17/851,897, filed on Jun. 28, 2022, now Pat. No. 11,642,118.

(Continued)

(51) Int. Cl.
    *A61B 17/02*     (2006.01)
    *A61B 5/00*     (2006.01)
    (Continued)

(52) U.S. Cl.
    CPC .......... *A61B 17/025* (2013.01); *A61B 5/4585* (2013.01); *A61B 17/149* (2016.11);
    (Continued)

(58) Field of Classification Search
    CPC ...................... A61B 2017/0268; A61B 5/4585
    See application file for complete search history.

(56) References Cited

U.S. PATENT DOCUMENTS

| | | | |
|---|---|---|---|
| 4,124,026 A | 11/1978 | Berner et al. | |
| 5,713,897 A | 2/1998 | Goble et al. | |
| (Continued) | | | |

FOREIGN PATENT DOCUMENTS

| | | |
|---|---|---|
| WO | 2014188184 | 11/2014 |
| WO | 2017195046 | 11/2017 |

OTHER PUBLICATIONS

Attune Knee System, CAS Surgical Technique, Published 2014, accessed at "http://synthes.vo.Ilnwd.net/o16/LLNWMB8/US%20Mobile/Synthes%20North%20America/Product%20Support%20Materials/Technique%20Guides/DSUS-JRC-0514-0141%20ATTUNE_CAS_ST.pdf".

(Continued)

*Primary Examiner* — David W Bates

(74) *Attorney, Agent, or Firm* — Shumaker, Loop & Kendrick LLP

(57)            ABSTRACT

A method of evaluating a human knee joint including a femur bone, a tibia bone, and ligaments. The method includes: inserting into the joint a tensioner-balancer that includes at least one force sensor; providing an electronic receiving device; moving the knee joint through at least a portion of its range of motion; using the electronic receiving device to collect data from the at least one force sensor; processing the collected force data to produce a digital geometric model of the knee joint, wherein the data includes: a medial spline representing a locus of points of contact of a medial condyle of the femur F with the tensioner-balancer, over a range of knee flexion angles; and a lateral spline representing the locus of points of contact of the femur F with the tensioner-balancer, over a range of knee flexion angles; and storing the digital geometric model for further use.

10 Claims, 31 Drawing Sheets

Related U.S. Application Data

(60) Provisional application No. 63/349,714, filed on Jun. 7, 2022.

(51) Int. Cl.

| | |
|---|---|
| *A61B 17/14* | (2006.01) |
| *A61B 17/15* | (2006.01) |
| *A61B 34/10* | (2016.01) |
| *A61B 34/20* | (2016.01) |
| *A61B 34/30* | (2016.01) |
| *A61B 17/00* | (2006.01) |

(52) U.S. Cl.
CPC ............ *A61B 17/154* (2013.01); *A61B 34/10* (2016.02); *A61B 34/30* (2016.02); *A61B 5/6885* (2013.01); *A61B 2017/00398* (2013.01); *A61B 2017/0268* (2013.01); *A61B 2034/105* (2016.02); *A61B 2034/2051* (2016.02)

(56) References Cited

U.S. PATENT DOCUMENTS

| | | | |
|---|---|---|---|
| 5,935,129 | A | 8/1999 | McDevitt et al. |
| 6,022,377 | A | 2/2000 | Nuelle et al. |
| 6,080,154 | A | 6/2000 | Reay-Young et al. |
| 6,162,234 | A | 12/2000 | Freedland et al. |
| 6,205,411 | B1 | 3/2001 | DiGioia, III et al. |
| 7,070,598 | B2 | 7/2006 | Lim et al. |
| 7,849,751 | B2 | 12/2010 | Clark et al. |
| 10,076,377 | B2 | 9/2018 | Bonutti et al. |
| 10,405,849 | B1 | 9/2019 | Cole et al. |
| 10,478,171 | B1 | 11/2019 | Cole et al. |
| 10,555,729 | B1 | 2/2020 | Cole et al. |
| 11,000,382 | B1 | 5/2021 | Cole et al. |
| 11,298,246 | B1* | 4/2022 | Cole ...................... A61B 34/20 |
| 11,642,118 | B1* | 5/2023 | Kellar ...................... A61F 2/46 606/9 |
| 11,826,057 | B1* | 11/2023 | Kellar .................... A61B 34/20 |
| 2001/0008971 | A1 | 7/2001 | Schwartz et al. |
| 2003/0032983 | A1 | 2/2003 | Bonutti et al. |
| 2004/0064191 | A1 | 4/2004 | Wasielewski |
| 2005/0222488 | A1 | 10/2005 | Chang et al. |
| 2005/0267485 | A1 | 12/2005 | Cordes et al. |
| 2008/0051798 | A1 | 2/2008 | Colquhoun et al. |
| 2008/0114367 | A1 | 5/2008 | Meyer |
| 2008/0288060 | A1 | 11/2008 | Kaye et al. |
| 2009/0299483 | A1* | 12/2009 | Amirouche .......... A61B 5/4528 623/20.29 |
| 2010/0007140 | A1 | 1/2010 | Duquette et al. |
| 2010/0249659 | A1* | 9/2010 | Sherman .............. A61B 17/025 600/587 |
| 2010/0250571 | A1 | 9/2010 | Pierce et al. |
| 2010/0256612 | A1 | 10/2010 | Dell'Oca |
| 2011/0093081 | A1 | 4/2011 | Chana et al. |
| 2012/0095515 | A1 | 4/2012 | Hamilton |
| 2013/0023795 | A1* | 1/2013 | Stein .................... A61B 5/4509 600/587 |
| 2013/0102929 | A1 | 4/2013 | Haight et al. |
| 2013/0131737 | A1 | 5/2013 | Cheng et al. |
| 2013/0226189 | A1 | 8/2013 | Young |
| 2014/0025081 | A1 | 1/2014 | Lorio et al. |
| 2014/0094715 | A1* | 4/2014 | Stein ...................... G01L 11/02 600/587 |
| 2014/0194907 | A1 | 7/2014 | Bonutti et al. |
| 2014/0257381 | A1 | 9/2014 | Palese |
| 2014/0277526 | A1 | 9/2014 | Stein et al. |
| 2014/0296979 | A1 | 10/2014 | Delfosse et al. |
| 2015/0105782 | A1 | 4/2015 | D'Lima et al. |
| 2016/0007909 | A1* | 1/2016 | Singh .................... A61F 2/4657 606/102 |
| 2016/0030156 | A1 | 2/2016 | Cole |
| 2016/0106409 | A1* | 4/2016 | Moholkar ............ A61B 5/4851 606/90 |
| 2016/0278944 | A1 | 9/2016 | D'Lima et al. |
| 2016/0338751 | A1 | 11/2016 | Kellar et al. |
| 2017/0035409 | A1 | 2/2017 | Fallin et al. |
| 2017/0065438 | A1 | 3/2017 | Burnikel |
| 2017/0172624 | A1 | 6/2017 | Brunner et al. |
| 2017/0312099 | A1* | 11/2017 | Paszicsnyek ............ A61F 2/38 |
| 2018/0049622 | A1 | 2/2018 | Ryan et al. |
| 2018/0116278 | A1 | 5/2018 | Lang |
| 2018/0153599 | A1 | 6/2018 | Daly et al. |
| 2018/0177612 | A1* | 6/2018 | Trabish .................. A61B 90/06 |
| 2018/0185100 | A1 | 7/2018 | Weinstein et al. |
| 2018/0199952 | A1 | 7/2018 | Cole |
| 2018/0296232 | A1 | 10/2018 | Nielsen et al. |
| 2019/0076273 | A1* | 3/2019 | Goodchild ........... A61B 5/6878 |
| 2019/0167447 | A1* | 6/2019 | Angibaud ............... A61F 2/389 |
| 2019/0183554 | A1 | 6/2019 | Pedicini |
| 2019/0200900 | A1* | 7/2019 | Thelen .................... A61B 8/42 |
| 2019/0224016 | A1 | 7/2019 | Walker et al. |
| 2019/0269526 | A1* | 9/2019 | Trabish ............... A61B 5/4585 |
| 2019/0358056 | A1 | 11/2019 | Lerat et al. |
| 2020/0155135 | A1* | 5/2020 | Cole ................. A61B 17/8869 |
| 2020/0237441 | A1 | 7/2020 | Zuhars et al. |
| 2021/0085305 | A1* | 3/2021 | Corpa De La Fuente .................. A61B 90/06 |
| 2022/0096222 | A1* | 3/2022 | Huff ...................... A61F 2/4657 |
| 2022/0362036 | A1 | 11/2022 | Rasmussen |

OTHER PUBLICATIONS

Bathis et al., "Flexion Gap Configuration in Total Knee Arthroplasty Following Hight Tibial Osteotomy", published online Sep. 30, 2004, International Orthopaedics (SICOT) 28: 366-369.

M. J. Winemaker, MD, FRCS (C), "Perfect Balance in Total Knee Arthroplasty, The Elusive Compromise", The Journal of Arthroplasty vol. 17. No. 1 2002, 2002, Churchill Livingstone, Canada.

International Search Report and Written Opinion from the International Searching Authority for International Patent Application No. PCT/US2019/061668 on Jan. 14, 2020.

International Search Report and Written Opinion from the International Searching Authority for International Patent Application No. PCT/US2021/018545 on May 6, 2021.

International Search Report and Written Opinion from the International Searching Authority for International Patent Application No. PCT/US2021/031961 on Sep. 10, 2021.

U.S. Appl. No. 17/851,931, filed Jun. 28, 2022 titled Machine Learning Based Joint Evaluation Method.

U.S. Appl. No. 17/851,869, filed Jun. 28, 2022 titled Knee Endoprothesis.

U.S. Appl. No. 17/851,948, filed Jun. 28, 2022 titled Knee Evaluation and Arthroplasty Method.

U.S. Appl. No. 17/881,410, filed Aug. 4, 2022 titled Joint Soft Tissue Evaluation Method.

* cited by examiner

KNEE TENSIONER-BALANCER AND METHOD

BACKGROUND

This invention relates generally to medical devices and instruments, and more particularly to a tensioner-balancer for a knee joint and methods for its use.

Total knee arthroplasty ("TKA") is a procedure for treating an injured, diseased, or worn human knee joint. In a TKA, an endoprosthetic joint is implanted, replacing the bearing surfaces of the joint with artificial members. Proper alignment of the joint and substantially equal tension in the soft tissues surrounding the joint are important factors in producing a good surgical outcome.

A human knee joint "J" is shown in FIGS. 1-4. The joint J is prepared for implantation by cutting away portions of the femur "F" and the tibia "T". FIGS. 1 and 2 show the joint in extension, with cutting planes for a tibial cut 1 and a distal femoral cut 2. The tibial cut 1 and the distal femoral cut 2 cooperate to define an extension gap "EG". FIGS. 3 and 4 show the joint J in flexion, with a cutting plane 3 shown for a posterior cut. The tibial cut 1 and the posterior cut 3 cooperate to define a flexion gap "FG".

FIG. 5 depicts an exemplary endoprosthesis 10 (i.e., implant) of a known type. The endoprosthesis 10 includes a tibial component 12 and a femoral component 14. The tibial component 12 is made up of a tibial tray 16 and an insert 18. The insert 18 has a back surface 20 which abuts the tibial tray 16 and an opposed articular surface 22. The tray includes a prominent keel 24 protruding in the inferior direction (i.e. down a longitudinal axis of the tibia). The tibial tray 16 may be made from a hard, wear-resistant material such as a biocompatible metal alloy. The insert 18 may be made from a low-friction material such as a bio-compatible plastic.

The femoral component 14 includes a back surface 28 shaped to abut a surface of the femur F that has been appropriately shaped and an articular surface 30 comprising medial and lateral condyles 32 and 34, respectively. The femoral component 14 may be made from a hard, wear-resistant material such as a biocompatible metal alloy.

The back surface 28 includes multiple faces collectively defining a rough "U" or "J" shape. The back surface 28 includes protruding locator pins 36.

The tibial tray 16 is implanted into the tibia T and the femoral component 14 is implanted into the femur F. The insert 18 is placed into the tibial tray 16. The articular surface 22 of the insert 18 bears against the articular surface 30 of the femoral component 14, defining a functional joint.

In the illustrated example, the endoprosthesis 10 is of the cruciate-retaining ("CR") type. It includes a cutout or notch 38 in the posterior aspect of the tibial component 12 which provides a space for the posterior cruciate ligament ("PCL").

A goal of total knee arthroplasty is to obtain symmetric and balanced flexion and extension gaps FG, EG (in other words, two congruent rectangles). These gaps are generally measured in millimeters of separation, are further characterized by a *varus* or valgus angle measured in degrees, and are measured after the tibia cut, distal femoral cut, and posterior femoral cut have been done (to create flat surfaces from which to measure). It follows that, to achieve this balance, the ligament tension in the lateral and medial ligaments would be substantially equal on each side or have a surgeon-selected relationship, and in each position.

One problem with prior art arthroplasty techniques is that it is difficult and complex to achieve the proper balance.

Current state-of-the-art gap balancing devices do not enable balancing with the patella in-place and are large, overly-complicated devices that work only with their respective knee implant systems.

BRIEF SUMMARY OF THE INVENTION

This problem is addressed by a tensioner-balancer (also referred to as a gap balancer, distractor, or distractor-tensioner) operable to measure characteristics of the joint such as a gap distance, angle between the bones, loads, and/or deflections, and optionally to apply a load to a gap between the bones of a joint (i.e., distract the joint).

According to one aspect of the technology described herein, a method is described of evaluating a human knee joint which includes a femur bone, a tibia bone, and ligaments, wherein the ligaments are under anatomical tension to connect the femur and tibia together, creating a load-bearing articulating joint. The method includes: inserting into the knee joint a tensioner-balancer that includes a femoral interface surface, and at least one force sensor; providing an electronic receiving device; moving the knee joint through at least a portion of its range of motion; while moving the knee joint, using the electronic receiving device to collect data from the at least one force sensor; processing the collected force data to produce a digital geometric model of the knee joint, wherein the data includes: a medial spline representing a locus of points of contact of a medial condyle of the femur F with the femoral interface surface, over a range of knee flexion angles; and a lateral spline representing the locus of points of contact of the femur F with the femoral interface surface over a range of knee flexion angles; and storing the digital geometric model for further use.

According to another aspect of the technology described herein, an apparatus for evaluating a human knee joint includes: a tensioner-balancer, including: a baseplate; a top plate defining a femoral interface surface, wherein the top plate includes a lateral cantilevered pad and a medial cantilevered pad, wherein each cantilevered pad is provided with one or more force transducers at the intersection between the respective cantilevered pad and a stationary portion of the top plate; a distracting mechanism interconnecting the baseplate and the top plate and operable to move the tensioner-balancer between retracted and extended positions; and wherein the top plate is pivotally connected to the distracting mechanism so as to be able to freely pivot about a pivot axis.

According to another aspect of the technology described herein, 20. An apparatus for machining bone includes: a robot arm having a plurality of arm segments interconnected with actuators operable to move the arm segments in response to command signals; the robot arm having a proximal end and a distal end configured for holding and manipulating an attachment; wherein the proximal end is configured to be coupled to a point of reference relative to a local coordinate system.

BRIEF DESCRIPTION OF THE DRAWINGS

The invention may be best understood by reference to the following description taken in conjunction with the accompanying drawing figures in which.

DETAILED DESCRIPTION OF THE INVENTION

Figures 1, 2:
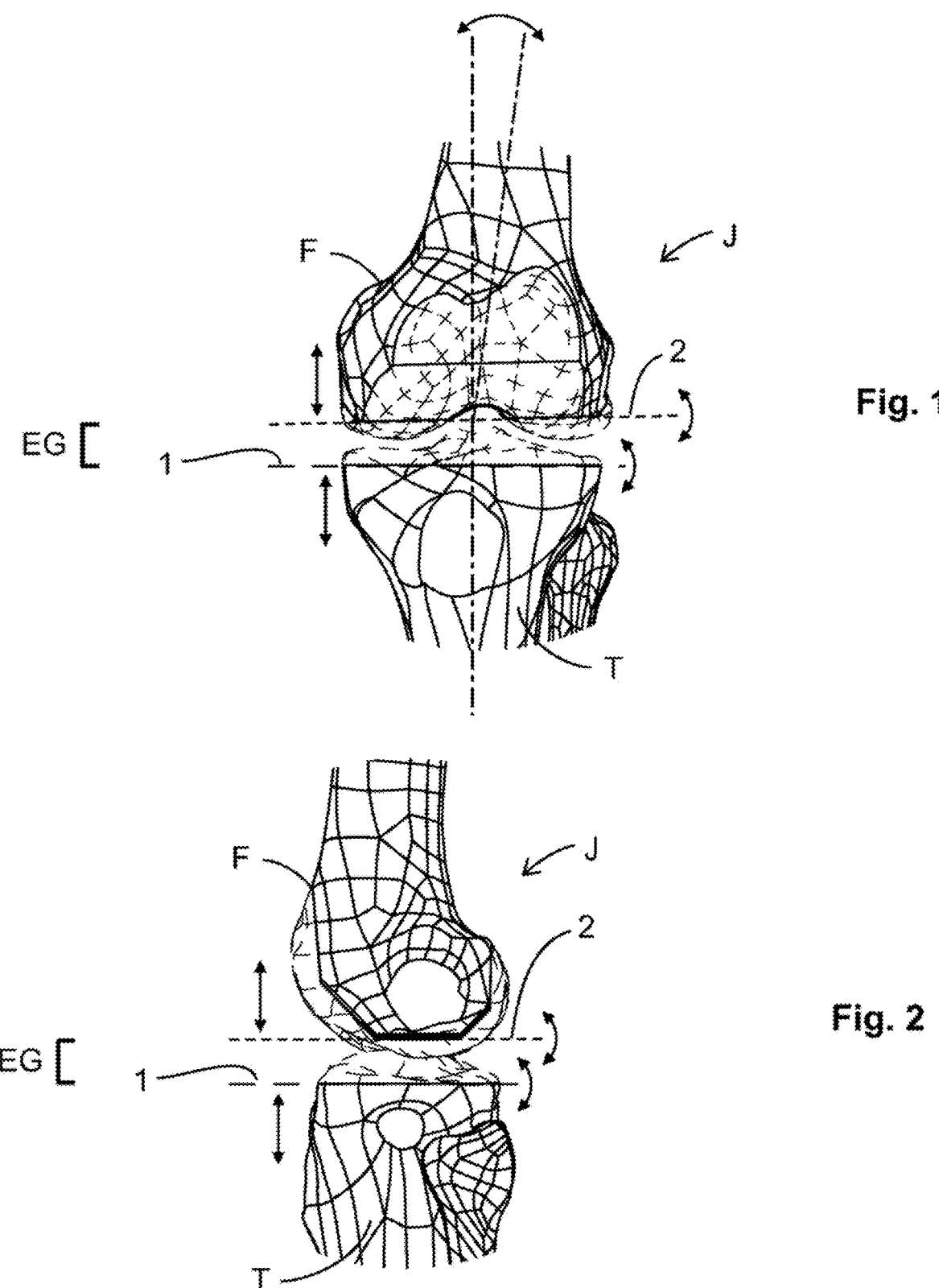
FIG. 1 is a view of the anterior aspect of the human knee joint in extension showing cutting planes for a total knee arthroplasty.
FIG. 2 is a view of the lateral aspect of the human knee joint of FIG. 1.
Figure 3:
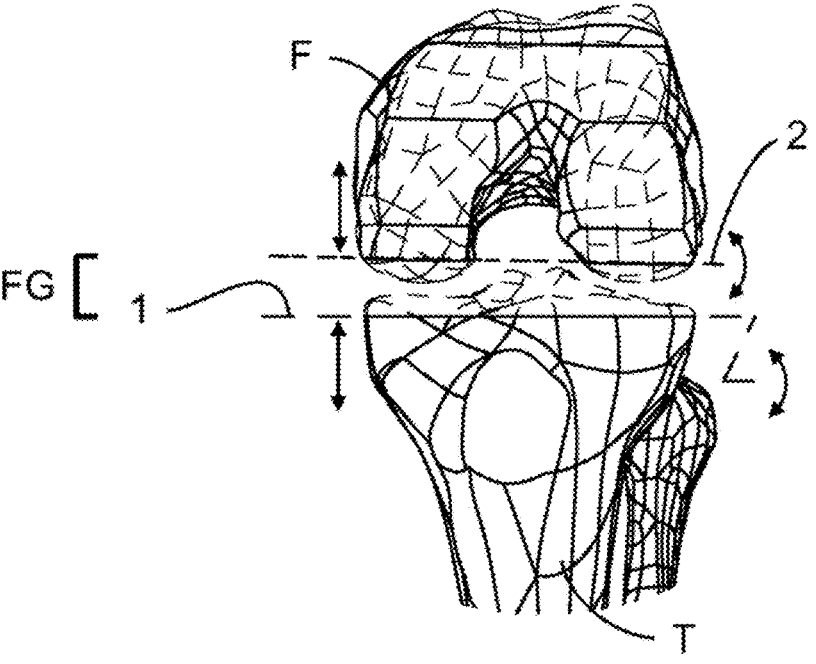
FIG. 3 is a view of the anterior aspect of the human knee joint in flexion showing cutting planes for a total knee arthroplasty.
Figure 4:
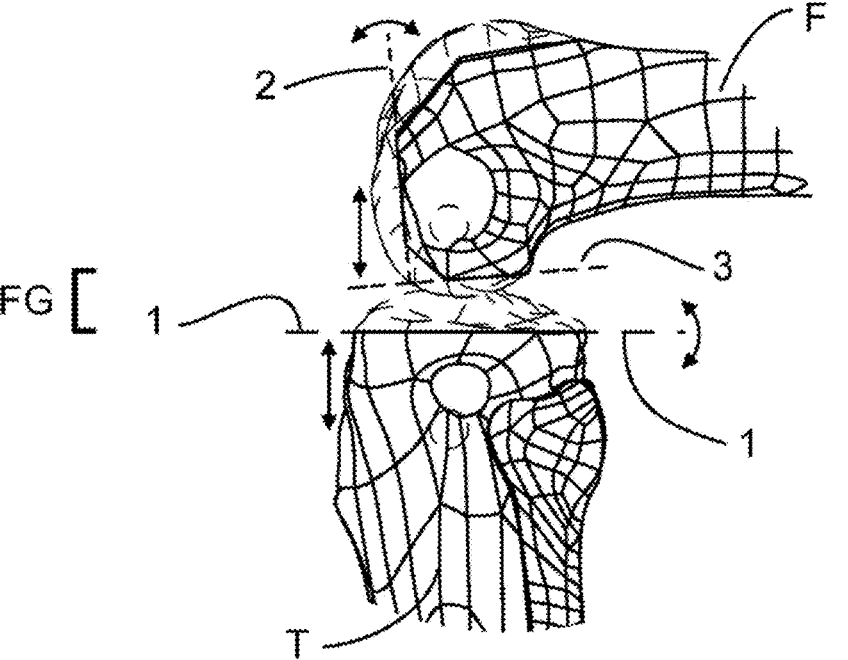
FIG. 4 is a view of the lateral aspect of the human knee joint of FIG. 3.
Figure 5:
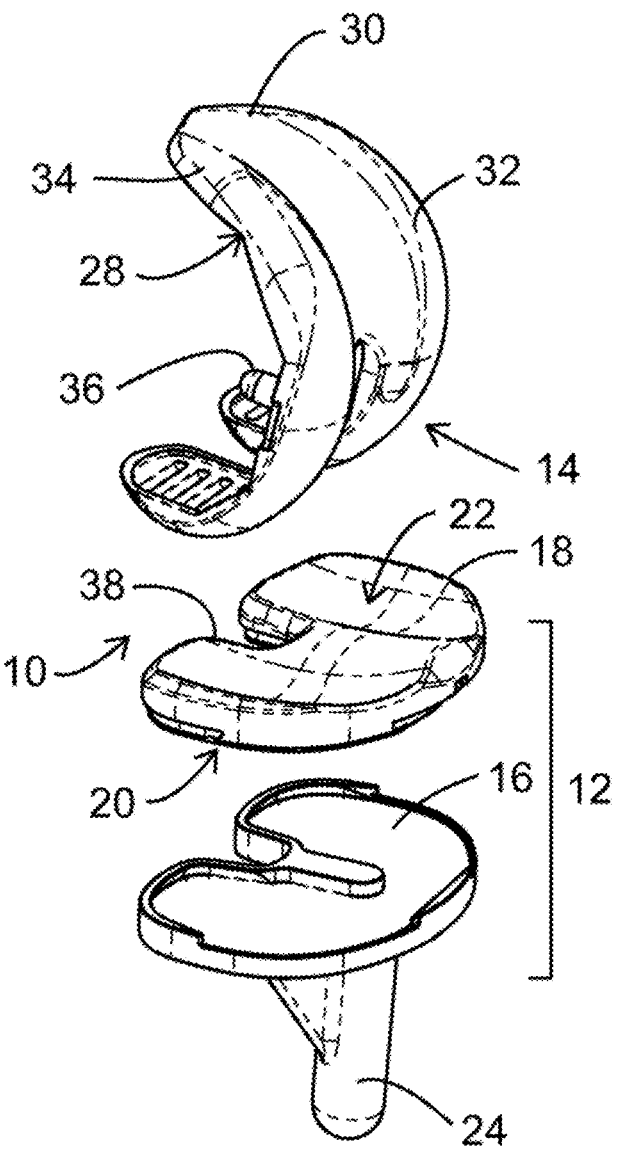
FIG. 5 is an exploded perspective view of a representative knee endoprosthesis.
Figure 6:
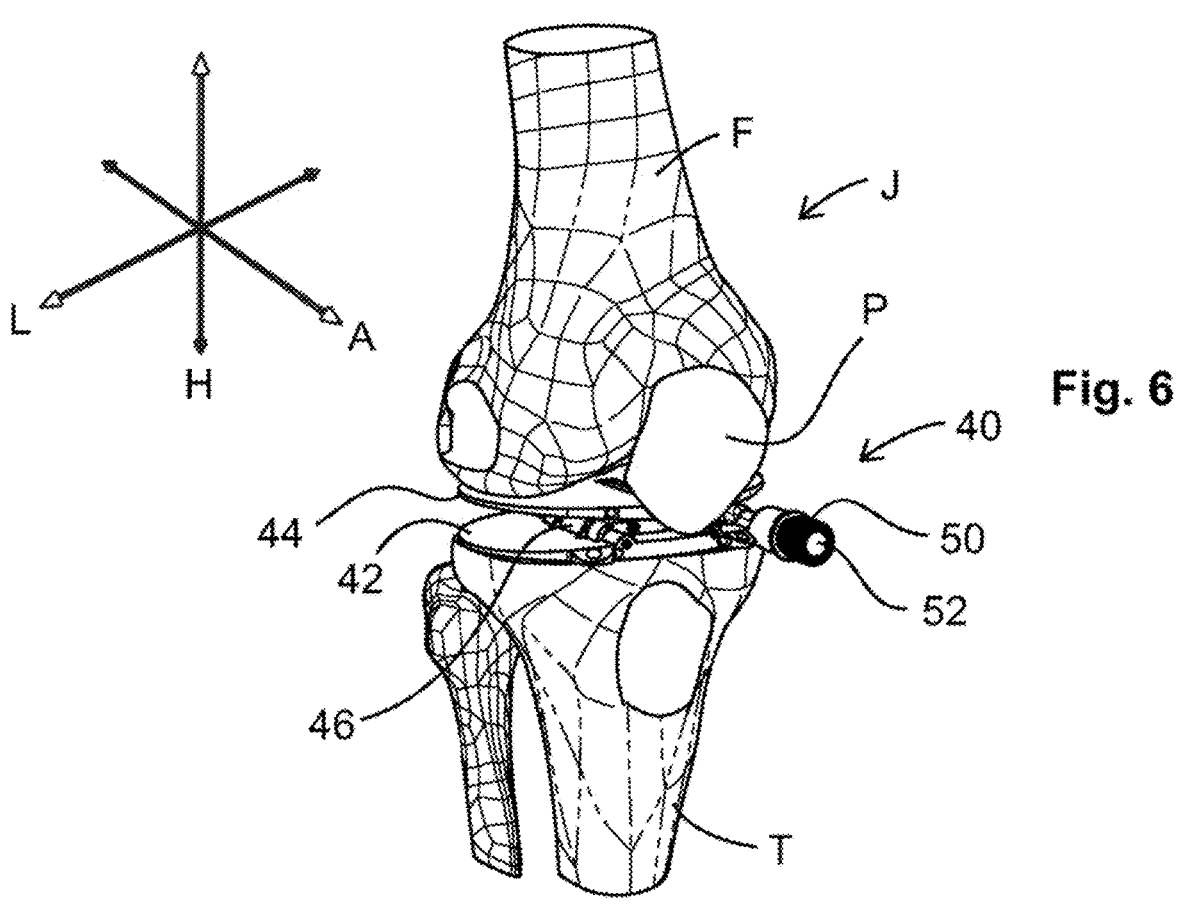
FIG. 6 is a perspective view of a human knee joint in an extended position, with a tensioner-balancer inserted therein.
Figure 7:
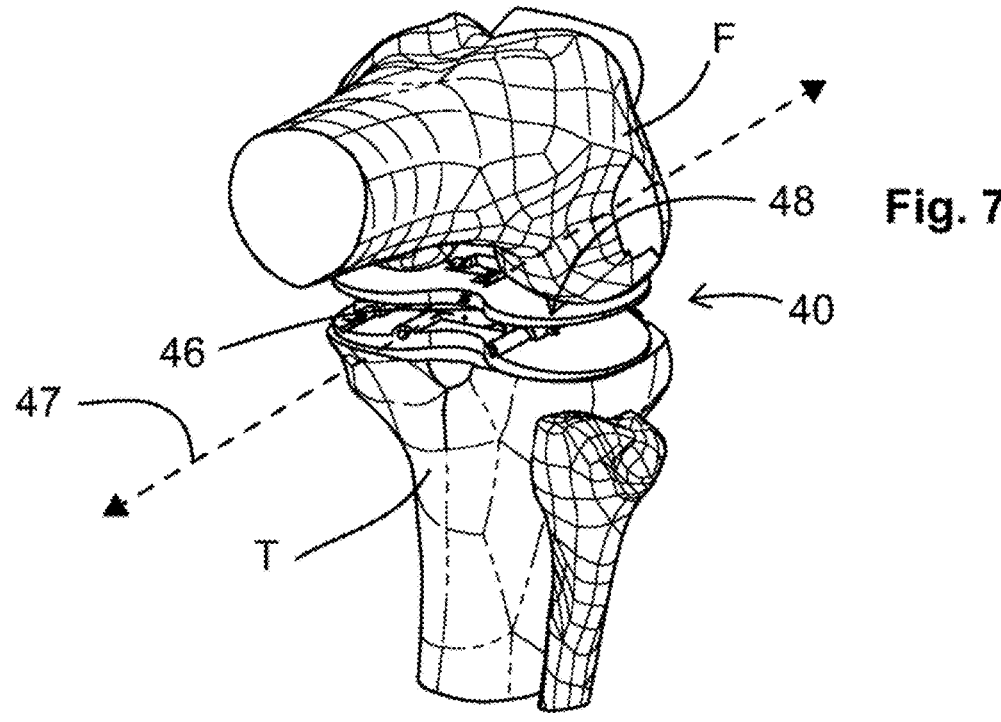
FIG. 7 is a view of the knee joint and tensioner-balancer of FIG. 6, in a flexed position.

Now, referring to the drawings wherein identical reference numerals denote the same elements throughout the various views, FIGS. 6 and 7 depict an exemplary embodiment of a tensioner-balancer 40 (alternatively referred to in various embodiments as a gap balancer, distractor, distractor-tensioner, or jack) which is useful for balancing a gap in a human knee joint as part of a total knee arthroplasty and for other therapeutic procedures.

Solely for purposes of convenient description, the tensioner-balancer 40 may be described as having a length extending along a lateral-to-medial direction "L", a width extending along an axial direction "A", and a height extending along a vertical direction "H", wherein the lateral direction, the axial direction, and the vertical direction are three mutually perpendicular directions. These directional terms, and similar terms such as "top", "bottom", "upper", "lower" are used merely for convenience in description and do not require a particular orientation of the structures described thereby.

In one aspect, the tensioner-balancer 40 may be described as having the ability to control the movement of one degree of freedom (e.g., translation along H) and measure the movement of a second degree of freedom (rotation about A) while constraining or fixing the remaining four degrees of freedom (translation along A and L; rotation about H and L).

The tensioner-balancer 40 comprises a baseplate 42 and a top plate 44 interconnected by a linkage 46. The linkage 46 and the tensioner-balancer 40 are movable between a retracted position in which the top plate 44 lies close to or against the baseplate 42, and an extended position in which the top plate 44 is spaced away from the baseplate 42. As described in more detail below, a means is provided to actuate the linkage 46 in response to an actuating force in order to separate the baseplate 42 and the top plate 44 in a controllable manner. This separation enables it to extend so as to apply a load to a knee joint. While the illustrated tensioner-balancer 40 includes a mechanically-operated linkage 46, it will be understood that this is just one operative example of a "distracting mechanism" operable to move the tensioner-balancer between retracted and extended positions. It is envisioned that the mechanical linkage could be replaced with other types of mechanical elements, or electrical, pneumatic, or hydraulic devices.

The top plate 44 includes a femoral interface surface 48 and is mounted to the linkage 46 in such a manner that it can freely pivot about pivot axis 47 (an axis corresponding to a varus/valgus angulation of the knee).

The baseplate 42 includes a tensioner-balancer coupler 50 having a first interface 52. In the illustrated example, the first interface 52 is configured as a socket. The coupler 50 is interconnected to the linkage such that an actuating force applied to the coupler 50, such as a torque, actuates the linkage 46.

Optionally, the tensioner-balancer 40 may incorporate means for measuring a force input. For example, the coupler 50 may incorporate a sensor (not shown) such as a strain gage operable to produce a signal representative of the torque applied to the coupler 50.

As a further option, the tensioner-balancer 40 may incorporate a separate measuring linkage (not shown) connected to the top plate and arranged to follow the movement of the top plate 44. The measuring linkage would be connected to a crank which would be in turn connected to a indicating shaft coaxial to the coupler. The measuring linkage may be arranged such that pivoting movement of the top plate results in rotation of the indicating shaft. The movement of the indicating shaft may be observed visually, or it may be detected by a sensor such as an RVDT or rotary encoder or resolver, which may be part of an instrument described below. This permits measurement of plate angle and/or vertical position.

The tensioner-balancer may be supplied with an appropriate combination of transducers to detect physical properties such as force, tilt angle, and/or applied load and generate a signal representative thereof. For example, the tensioner-balancer may be provided with sensors operable to detect the magnitude of extension (i.e. "gap height"), the angle of the top plate about the pivot axis 47 (i.e. varus/valgus), and/or the applied force in the extension direction. Nonlimiting examples of suitable transducers include strain gages, load cells, linear variable differential transformers ("LVDT"), rotary variable differential transformers ("RVDT"), or linear or rotary encoders or resolvers.

Figure 8:
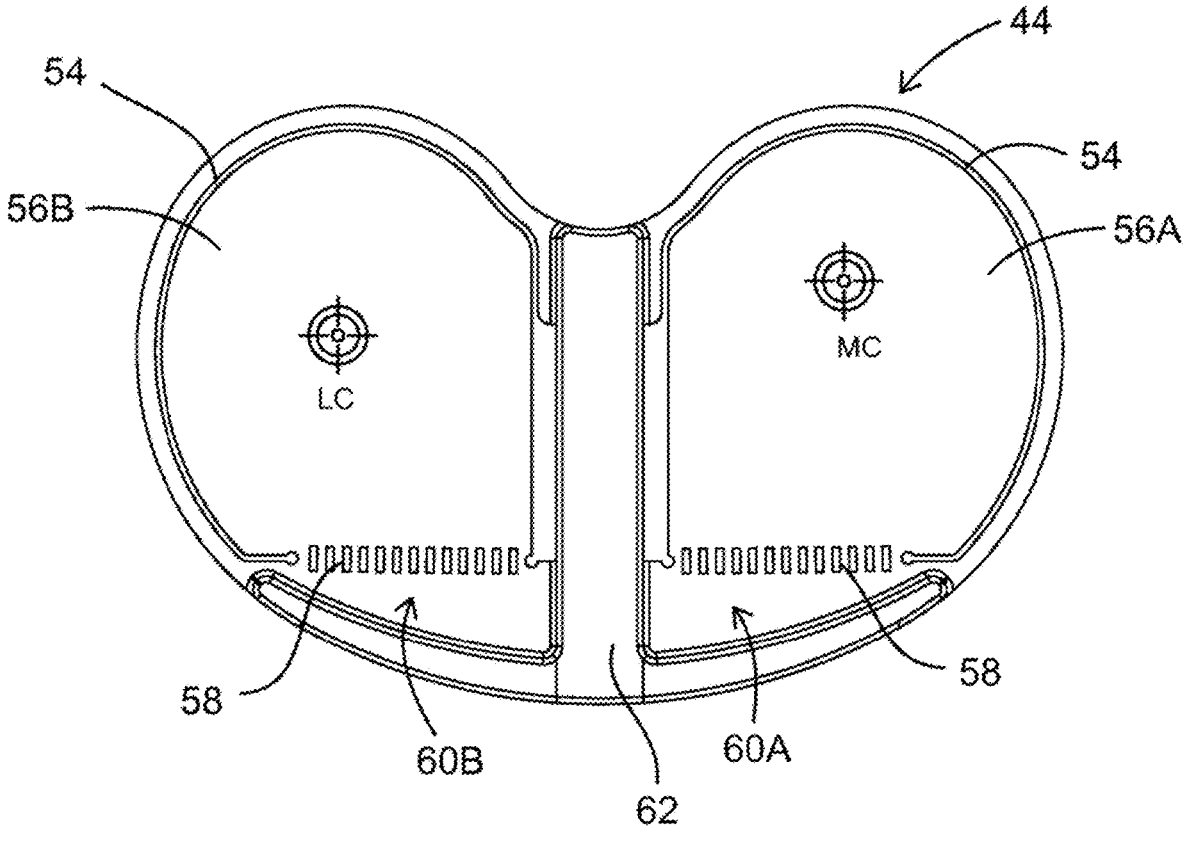
FIG. 8 is a top plan view of a top plate of the tensioner-balancer of FIG. 6.
Figure 9:
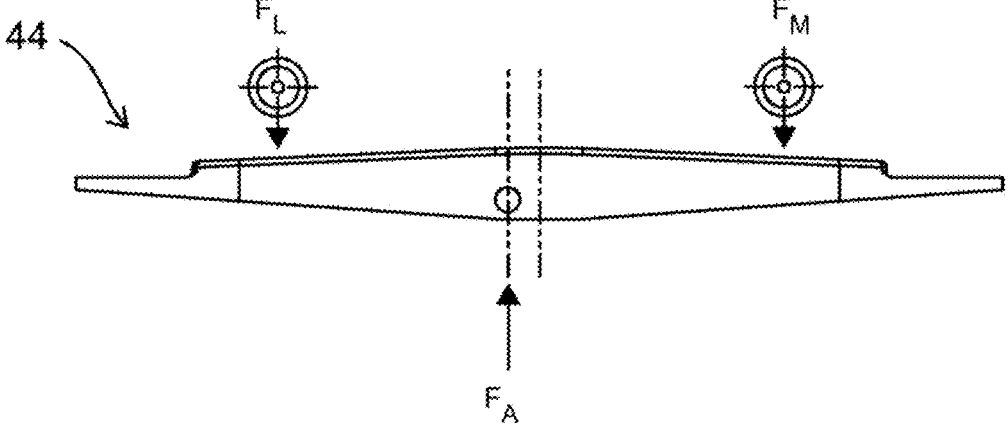
FIG. 9 is a front elevation view of the top plate of FIG. 8.

FIGS. 8 and 9 illustrate an exemplary configuration in which the top plate 44 includes grooves 54 which define medial and lateral cantilevered pads 56A, 56B respectively. Two or more spaced-apart strain gages 58 are mounted to the top plate 44 in a first left-right row 60A at the intersection between the medial pad 56A and the forward portion 62 of the top plate 44. Two or more spaced-apart strain gages 58 are mounted to the top plate 44 in a second fore-aft row 60B at the intersection between the lateral pad 56B and the forward portion 62 of the top plate 44.

Figure 10:
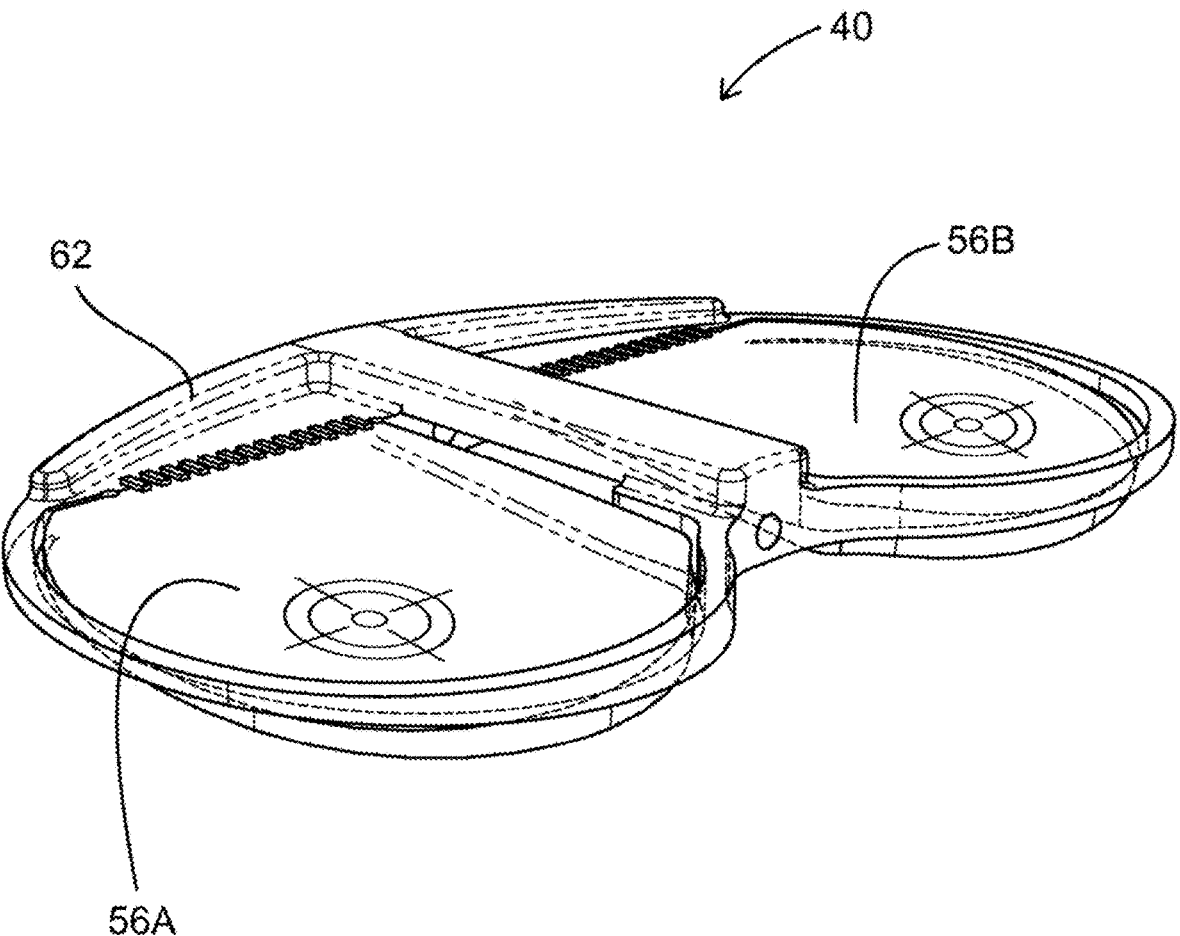
FIG. 10 is a perspective view of the top plate of FIG. 8, in a deflected position.

FIG. 10 shows the medial and lateral cantilevered pads 56A, 56B in a deflected position under load. The magnitude of deflection is greatly exaggerated for illustrative purposes.

Referring to FIG. 8, when the knee joint is articulated it is possible to identify an instantaneous point of peak contact pressure. There is one such point for each of the condyles. These positions are mapped onto the medial and lateral cantilevered pads 56A, 56B and labeled "MC" (standing for "medial load center") and "LC" (standing for "lateral load center").

Figure 11:
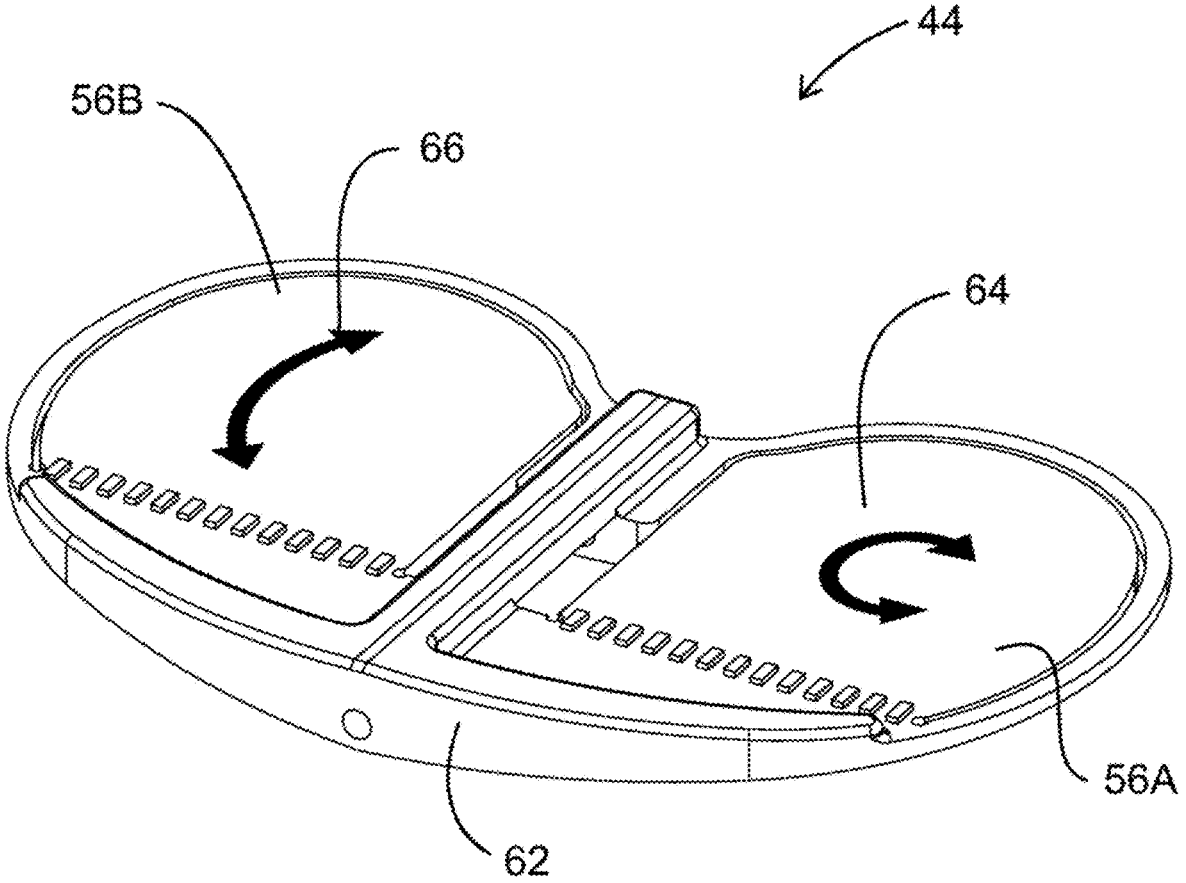
FIG. 11 is a perspective view of the top plate of FIG. 8, showing movement of contact points superimposed thereon.

Analysis by the inventors has shown that using the depicted configuration, with at least two spaced-apart strain gauges provided for each of the cantilevered pads 56A, 56B, it is possible to resolve the position of the load centers MC, LC in two axes. Stated another way, using this hardware, it is possible to identify the instantaneous lateral-medial and anterior-posterior position of the load centers LC, MC. Referring to FIG. 11, and as will be described further below, this enables the ability of the tensioner-balancer 40 to track certain relative movements of the femur F. One of these is referred to as "medial pivot" shown by arrow 64 and the other is referred to as "rollback", shown by arrow 66.

Figure 12:
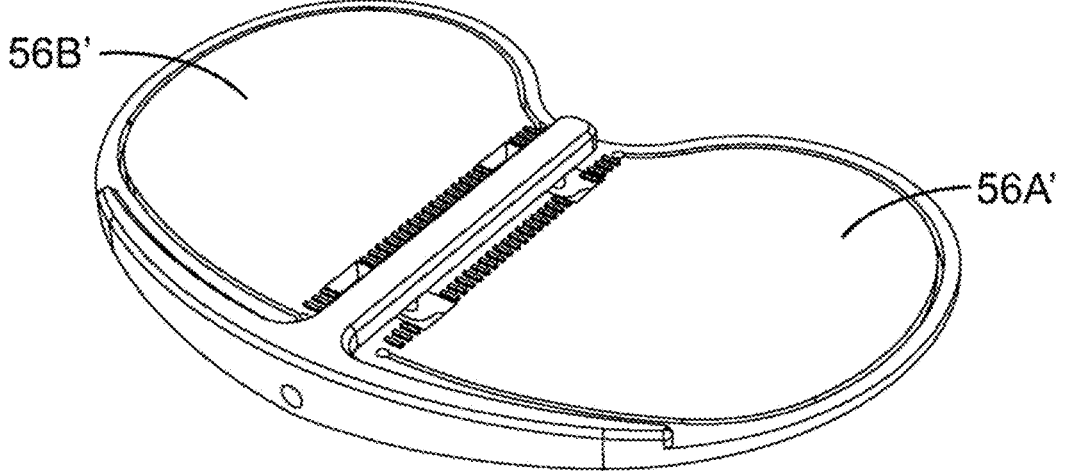
FIG. 12 is a perspective view of an alternative top plate configuration of the tensioner-balancer of FIG. 6.
Figure 13:
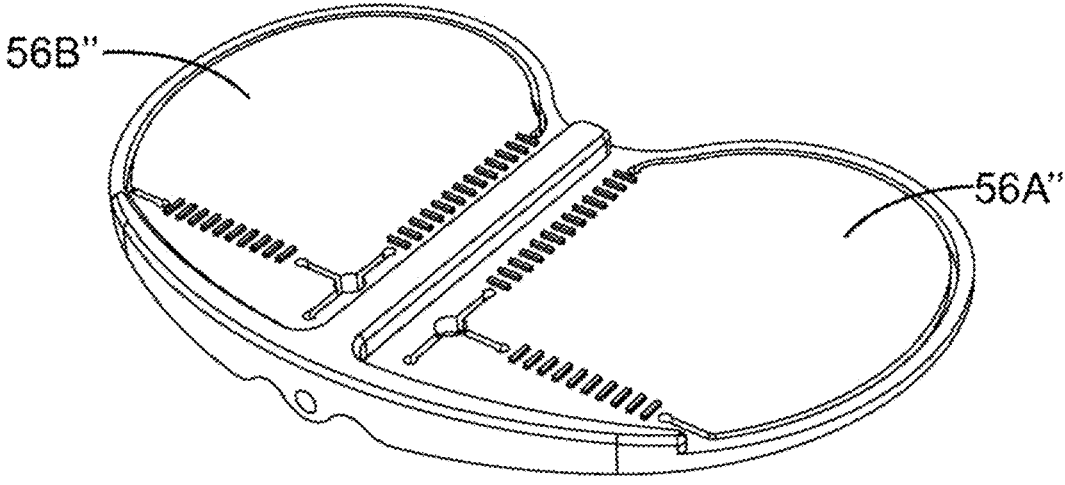
FIG. 13 is a perspective top plan view of an alternative top plate configuration of the tensioner-balancer of FIG. 6.

Various physical configurations of the top plate with cantilevered pads are possible with similar functionality. For example, FIG. 12 illustrates medial and lateral cantilevered pads 56A', 56B' which are cantilevered along an anterior-posterior axis (as opposed to a lateral-medial axis as shown in FIGS. 8-10). As another example, FIG. 13 illustrates medial and lateral cantilevered pads 56A", 56B" which are cantilevered along both an anterior-posterior axis and a lateral-medial axis. As another alternative (not separately illustrated), the lateral pad could be cantilevered along one axis and the medial pad could be cantilevered along a different axis.

Figure 14:
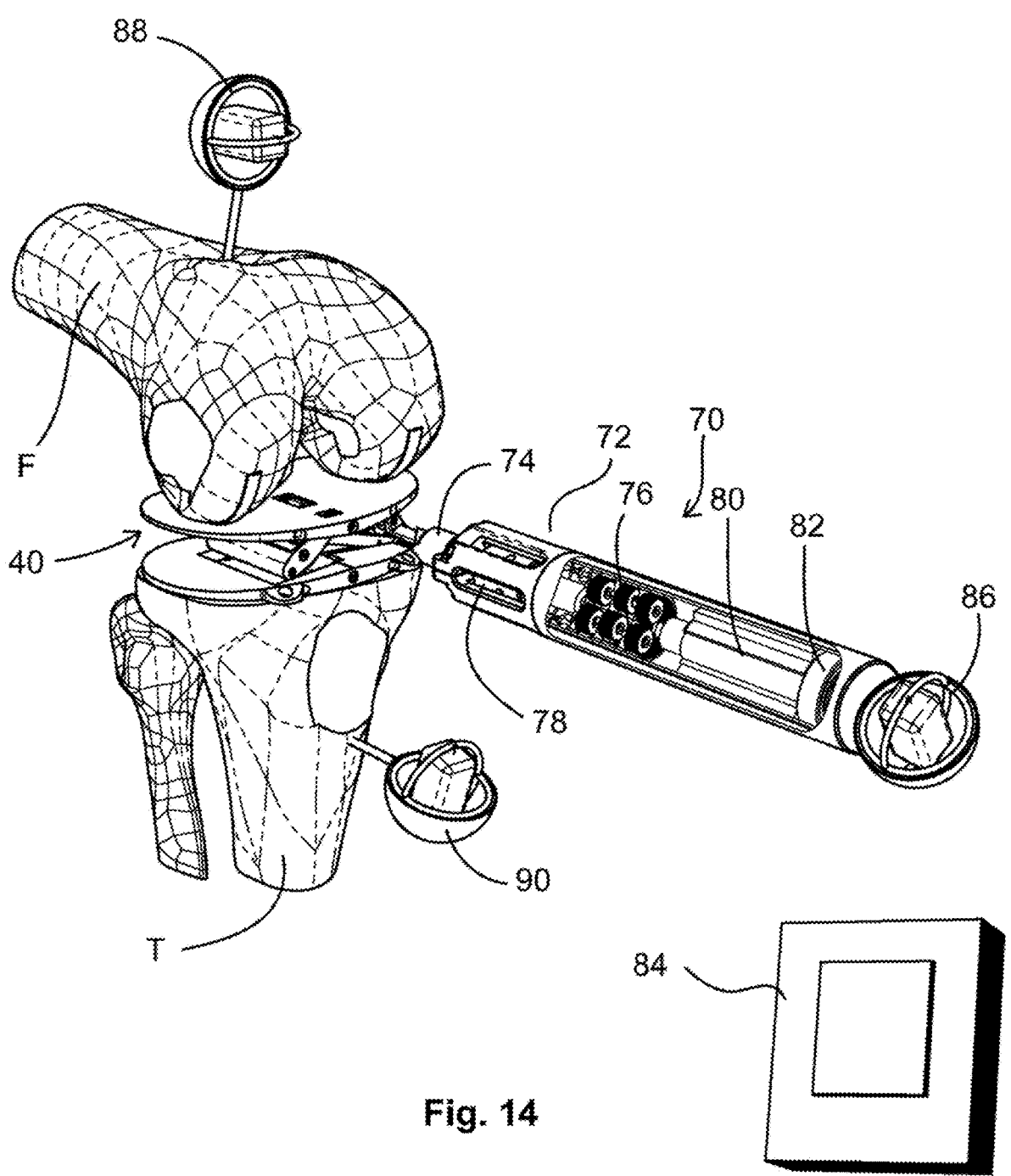
FIG. 14 is a perspective view of the human knee joint with a tensioner-balancer inserted therein and coupled to a instrument.

FIG. 14 illustrates an exemplary actuating instrument 70 for use with the tensioner-balancer 40. The actuating instrument 70 includes a barrel 72 with an instrument coupler 74 at its distal end defining a second interface (hidden in this view) which is complementary to the first interface 52 of the tensioner-balancer 40. The interior of barrel 72 includes an appropriate internal mechanism to apply torque to the instrument coupler 74 through a shaft 78, such as a stepper motor 80 with related control electronics including a rotary encoder coupled to a planetary gearset 76 that interconnects the stepper motor 80 and shaft 78.

The internal mechanism is operable to apply an actuating load to the tensioner-balancer 40. The actuating instrument 70 includes an electronic data transceiver, shown schematically at 82. The transceiver 82 may operate over a wired or wireless connection. The actuating instrument 70 may be supplied with an appropriate combination of transducers (not shown in FIG. 14) to detect physical properties such as force, tilt angle, and/or applied load and generate a signal representative thereof. For example, the tensioner-balancer 40 may be provided with sensors operable to detect the magnitude of extension (i.e. "gap height"), the angle of the top plate about the pivot axis (i.e. varus/valgus), and/or the applied force in the extension direction. Nonlimiting examples of suitable transducers include strain gages, load cells, linear variable differential transformers ("LVDT"), rotary variable differential transformers ("RVDT"), or linear or rotary encoders or resolvers.

Displacement of the tensioner-balancer 40 may be derived from the encoder signals, knowing the kinematics of the linkage 46. The transceiver 82 is operable to transmit the signal.

A remote display 84 is configured to receive the signal and produce a display of the transducer data. As one example, the remote display 84 may be embodied in a conventional portable electronic device such as a "smart phone" or electronic tablet with suitable software programming. Optionally, the remote display 84 or other suitable transmitting device may be used to send remote operation commands to the actuating instrument 70.

In use, the remote display 84 permits the surgeon to observe the physical properties of the tensioner-balancer 40 in real time as the actuating instrument 70 is used to operate the tensioner-balancer 40.

Optionally, the actuating instrument 70 may incorporate a tracking marker 86. The tracking marker 86 is operable such that, using an appropriate receiving device, the position and orientation of the receiving device relative to the tracking marker 86 may be determined by receipt and analysis at the receiving device of signals transmitted by the tracking marker 86.

The function of the tracking marker is to provide six degree of freedom (6-DOF) position information in a local coordinate reference space (i.e., position and orientation in each of three mutually perpendicular axes). Some devices or systems may be able to provide 6DOF position information without requiring line of sight for signals (e.g., electromagnetic spectrum energy). For example, as illustrated, the tracking marker 86 may be configured as an inertial navigation device including one or more accelerometers and gyroscopic elements capable of providing angular rate information and acceleration data in 3D space.

In an alternative embodiment which is not illustrated, the tracking marker may include one or more tracking points which may be configured as transmitting antennas, radio-logical markers, or other similar devices. This type of tracking marker may make use of line of sight transmission of signals to determine position.

Tracking markers 86 and appropriate receivers are known within the state-of-the-art.

A tracking marker 88 would be attached to the femur F in such a way that it has a substantially fixed position and orientation relative to the femur F. For example, a tracking marker 88 may be attached directly to the femur F.

In addition to the femur-mounted tracking marker 88, at least one additional tracking marker is provided which has a substantially fixed position and orientation relative to the tibia T. Where the actuating instrument 70 is rigidly coupled to the tensioner-balancer 40, the tibial tracking function may be provided by the tracking marker 86 of the actuating instrument 70. Alternatively, a tracking marker 90 may be attached directly to the tibia T.

Figures 15, 16:
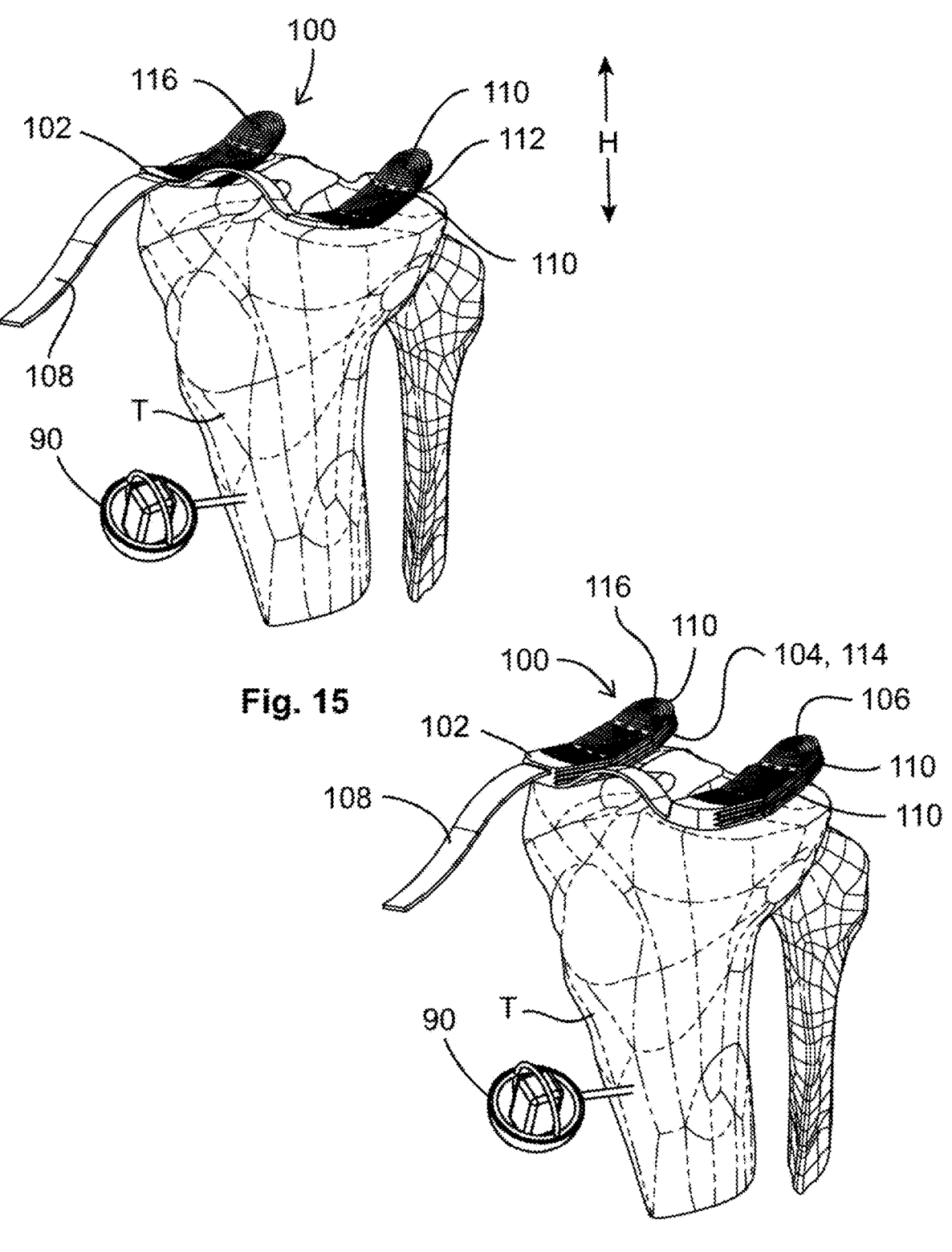
FIG. 15 is a perspective view of a portion of a human knee joint with an alternative tensioner-balancer disposed of thereon, in a retracted position.
FIG. 16 is a view of the knee joint and tensioner-balancer of FIG. 15, in an extended position.

FIGS. 15 and 16 show another embodiment of a tensioner-balancer 100. The tensioner-balancer 100 comprises a body 102 with a tibial interface surface 104 and an opposed femoral interface surface 106. The tensioner-balancer 100 is generally U-shaped in plan form. It may include a coupler 108 providing electrical, fluid, and/or mechanical connections.

Generally, the overall thickness of the tensioner-balancer 100 (i.e., measured in direction H) may be on the order of one or two millimeters. This enables the tensioner-balancer 100 to be inserted into a knee joint J without first having to distract the joint or cut away any tissue.

The body 102 may be divided into a plurality of segments 110 which may be hinge elements 112 (e.g., live hinge strips) to allow the segments 110 to flex or pivot relative to each other. Each of the segments 110 may take the form of an expandable hollow chamber which may be inflated by fluid pressure or other means such as discrete electromechanical actuation, for example applying an electrical charge to a superelastic or memory metal. FIG. 15 shows the segments 110 in a deflated or retracted position. FIG. 16 shows the segments 110 in an inflated or extended position. The walls forming the segments 110 may be configured as an "accordion" or "corrugated" structure to permit them to selectively expand or collapse into a compact size.

An array of tibial force sensors 114 are attached to or integrated into the tibial interface surface 104. They may be arranged in a pattern such as a grid layout or a radial layout.

An array of femoral force sensors 116 are attached to or integrated into the femoral interface surface 106. They may be arranged in a pattern such as a grid layout or a radial layout.

Each of the force sensors 114, 116 includes one or more transducers operable to detect an applied force and produce a signal representative of (e.g., proportional to) the applied force and/or pressure. Optionally, each of the force sensors 114, 116 may detect and produce a signal representative of (e.g., proportional to) displacement and/or position (e.g., height). Nonlimiting examples of transducers effective to produce a signal include strain gauges, or miniature linear variable differential transformers (LVDT), or piezoelectric transducers. The force sensors are segmented into at least a 2D or two-axis array of sensor elements, e.g., a matrix which is addressable by X, Y reference, radial coordinates, or other suitable position location. The size of the individual sensor elements in the arrays may be selected as required to produce useful and actionable information.

The sensor arrays may be connected to an electronic receiving device as described elsewhere herein by a wired or wireless connection. Appropriate processors and software may be provided for interpretation of the signals from the sensor arrays.

Figure 17:
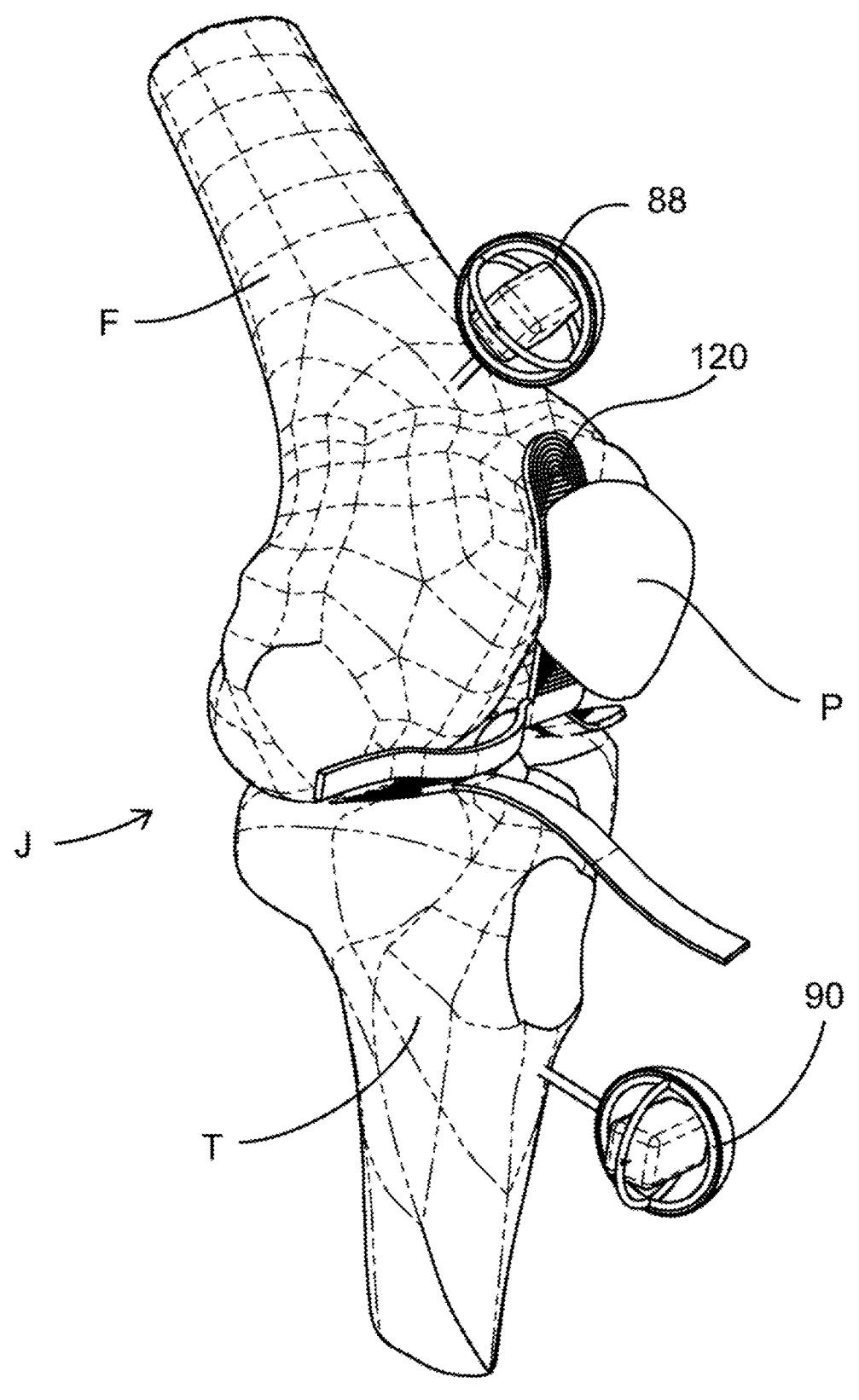
FIG. 17 is a perspective view of a human knee joint with a load cell disposed contact with the patella.

In addition to collecting force, pressure, and/or displacement data between the femur F and the tibia T, an additional device may be used to collect force, pressure, and/or displacement data between the femur F and the patella P. FIG. 17 shows a human knee joint J in flexion. A patella force sensor 120 is shown disposed between the patella P and the femur F. The patella force sensor 120 may include one or more individual sensors operable to detect force, pressure, and/or displacement and produce representative signals, as described above with respect to the sensors of the gap balancer embodiments. This data may be transmitted through a flexible cable as shown in FIG. 15, or over a wireless connection.

Figure 18:
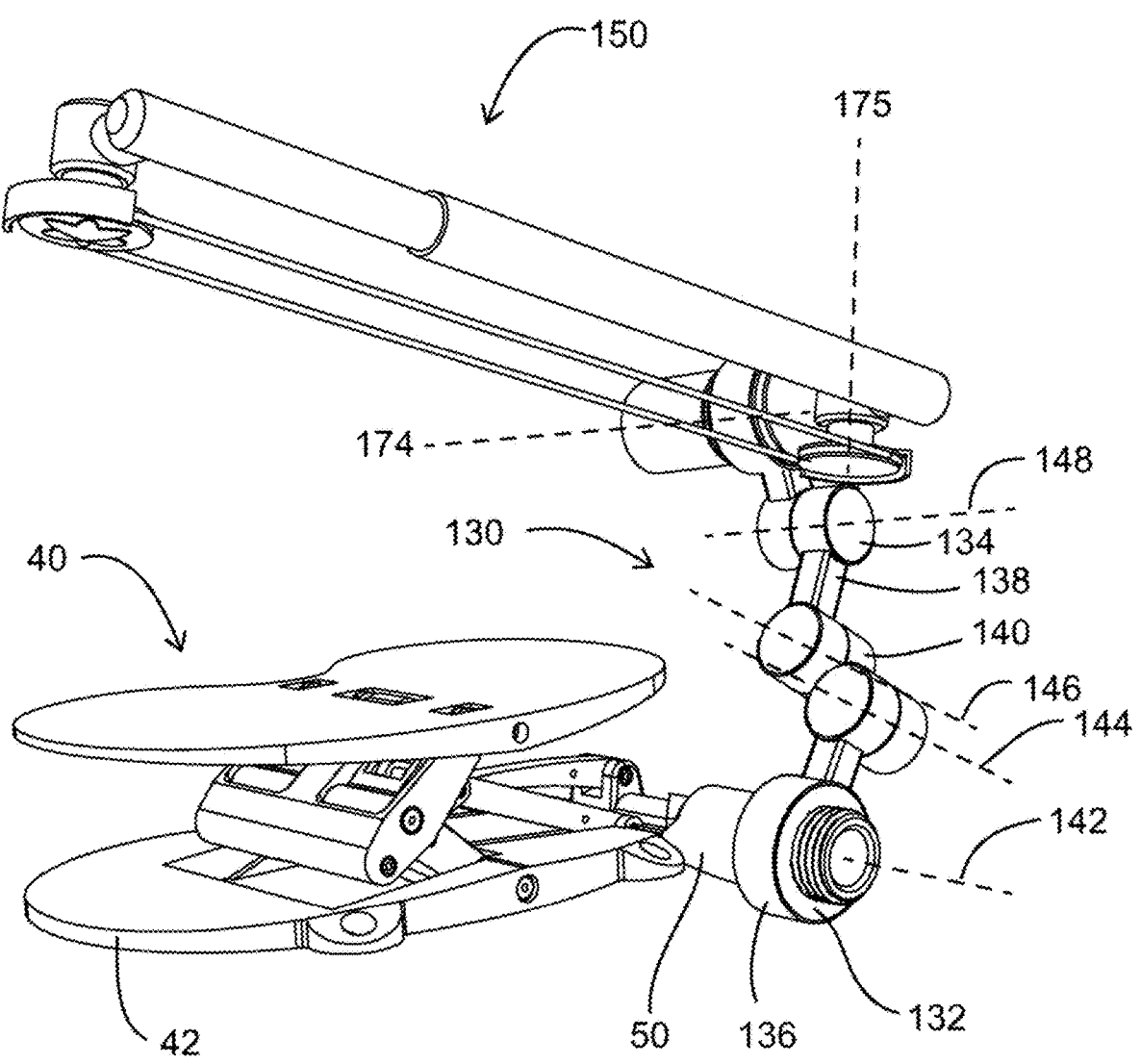
FIG. 18 is a perspective view of an exemplary robot arm coupled to a tensioner-balancer.

The utility of the tensioner-balancer 40 may be extended by various attachments. As an example, FIG. 18 illustrates a robot arm 130 adapted for use with the tensioner-balancer 40. The robot arm 130 extends between a proximal end 132 and a distal end 134. The proximal end includes a mount 136 which permits the robot arm 130 to be coupled to the tensioner-balancer 40 or another suitable object. The robot arm 130 includes a number of arm segments 138 interconnected with actuators 140 of a known type capable of rotating the arm segments 138 to desired positions in response to command signals. In the illustrated example, the robot arm 130 includes actuators sufficient to produce motion about four separate axes labeled 142, 144, 146, and 148, respectively. This motion can be controlled relative to the local coordinate system established by the local tracker connected to the tensioner-balancer baseplate or femur or tibia (not shown).

The robot arm 130 is suitable for holding and manipulating various attachments coupled to the distal end 134, including but not limited to: a saw, a drill, a retractor, a mechanical (i.e. drill, saw) or visual guide or a physical cutting guide for a surgeon, and/or an implant (endoprosthesis).

Figures 19, 20, 21, 22:
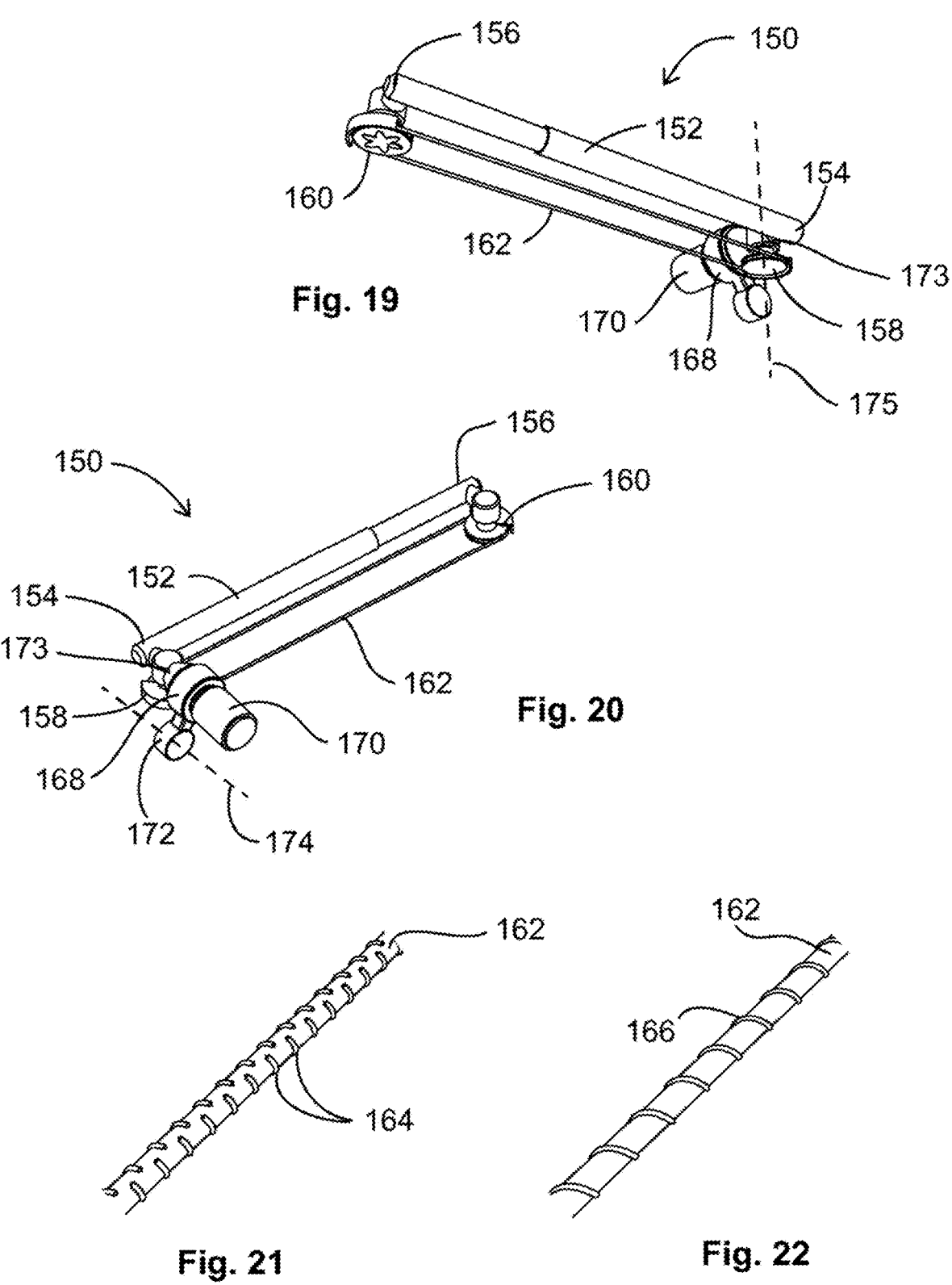
FIG. 19 is a perspective view of an exemplary cable saw.
FIG. 20 is another perspective view of the cable saw of FIG. 19.
FIG. 21 is a perspective view of a section of an exemplary cable for the saw of FIG. 19.
FIG. 22 is a perspective view of a section of an alternative cable for the saw of FIG. 19.

FIGS. 19 and 20 Illustrate a cable saw 150 for use with the robot arm 130. For example, the cable saw 150 can be used to make a distal femur cut, posterior femur cut, anterior femur cut, patellar surface cut, and/or femoral chamfer cuts.

The cable saw 150 includes a beam 152 extending between a first end 154 and a second end 156. A drive pulley 158 is disposed at the first end 154 and an idler pulley 160 is disposed at the second end 156. The beam 152 is configured so that it can adjust the distance between the two pulleys and/or apply a selected amount of tension. In the illustrated example the beam 152 comprises two telescoping sections. The beam 152 includes some means for changing the overall length of the telescoped sections, such as an internal threaded adjustment, an internal actuator, or one or more springs (not shown).

A cutting cable 162 runs over the pulleys 158, 160 in a closed loop. The cutting cable 162 includes one or more cutting elements such as protruding ridges or teeth 164 shown in FIG. 21 or a continuous spiral ridge 166 shown in FIG. 22. Optionally, the cutting cable 162 may incorporate or be coated with an abrasive substance and/or a substance to minimize the increase in temperature associated with cutting. The tension on the cutting cable 162 is sent by adjusting the overall length of the beam 152 as described above. Additionally, the cutting cable may be immersed in a stream of biocompatible cutting fluid to reduce the time and temperature of the machining process (i.e. cold saline) supplied by a targeted nozzle or by dripping from the housing directly onto the wire saw.

The drive pulley 158 is coupled to an appropriate rotary driver 168 such as an electric motor or pneumatic motor (shown schematically). The rotary driver 168 is in turn coupled to a mount 170 which permits the cable saw 150 to be coupled to the robot arm 130. Optionally, a rotary actuator 172 may be disposed between the rotary driver 168 and the mount 170. The actuator may be a known type capable of rotating to desired positions in response to command signals. This permits the beam 152 to be rotated about an axis 174. Optionally, a rotary actuator 173 may be disposed between the rotary driver 168 and the beam 152. This permits the beam 152 to be rotated about an axis 175 parallel to the axis of rotation of the drive pulley 158.

Figure 23:
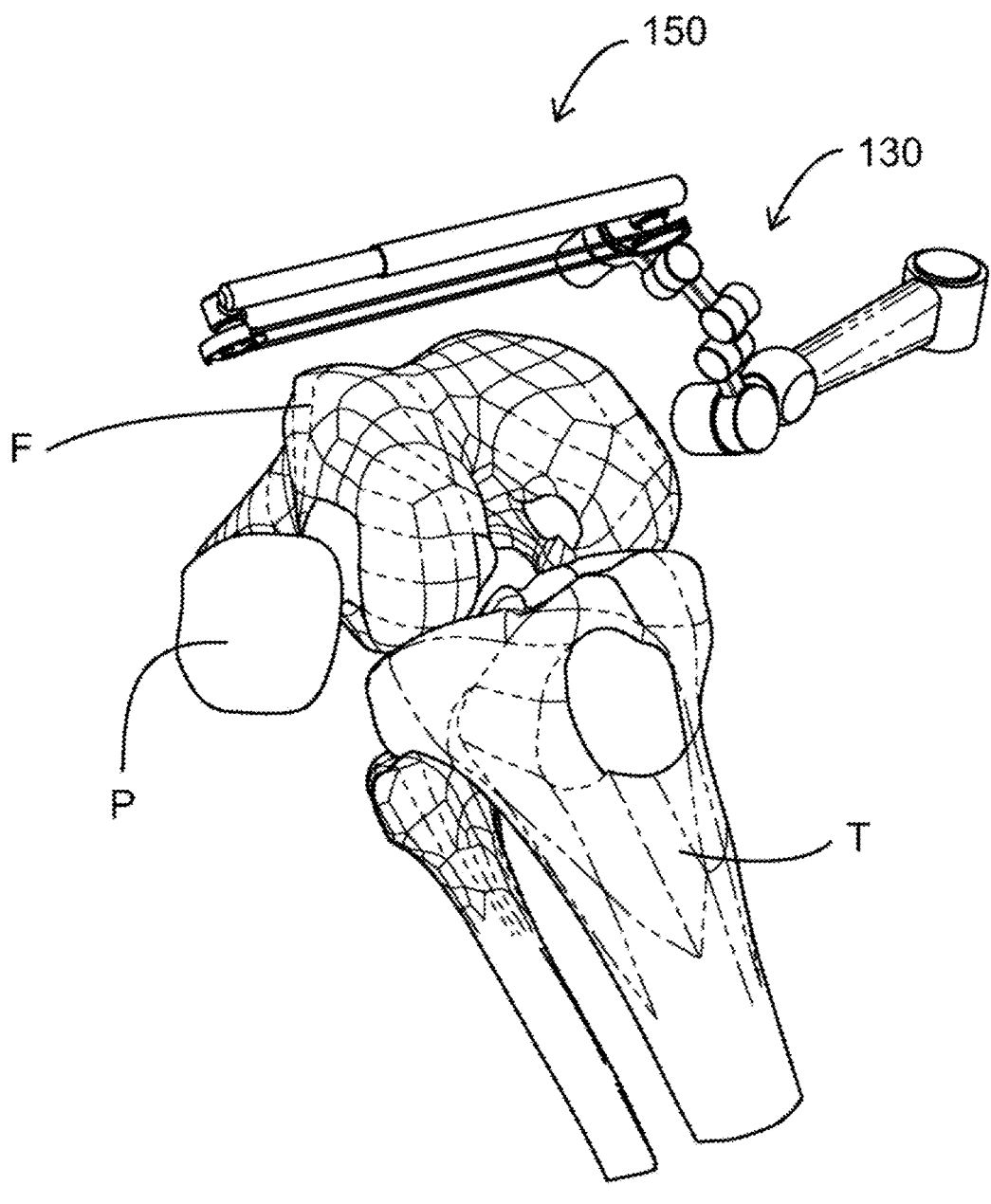
FIG. 23 is a perspective view of a cable saw and robot arm in proximity to a human knee joint.

In the example shown in FIG. 18, the complete structure consisting of the robot arm 130 and the attached cable saw 150 has mobility about a total of six axes. The assembled and articulated robot arm 130 and cable saw 150 are capable of making different cuts in the knee joint J as shown in FIG. 23.

Figure 24:
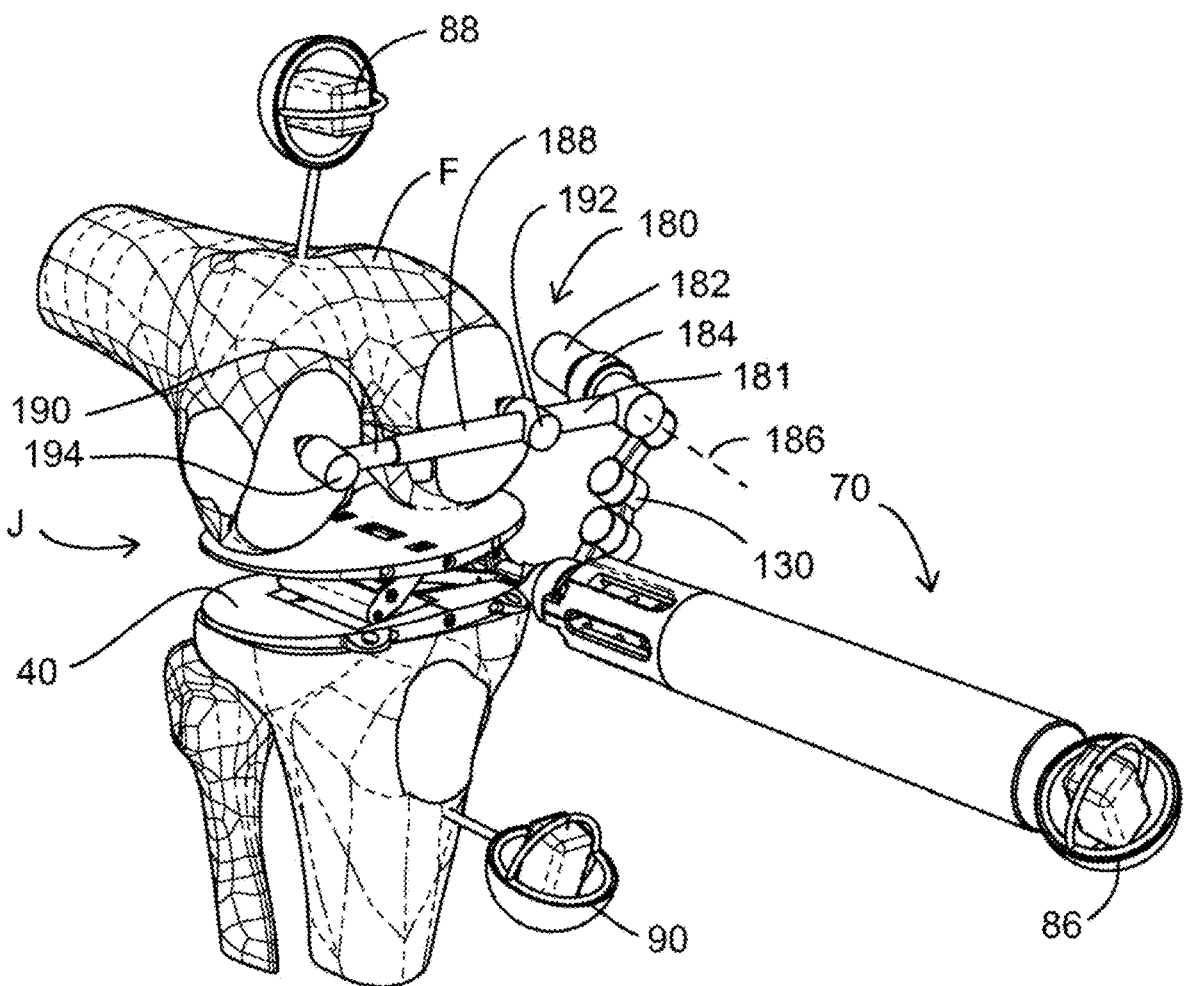
FIG. 24 is a perspective view of a tensioner-balancer and robot arm inserted into human knee joint, in combination with a spotting apparatus.

Another example of a robot arm attachment is a spotting apparatus 180 seen in FIG. 24. This comprises a bar 181 extending from an articulated mount 182 which is in turn coupled to the robot arm 130. The mount 182 includes an actuator 184 permitting the bar 180 to pivot about a first axis 186. The bar 181 is formed in two telescoping sections 188, 190 which may be extended or retracted using an internal actuator (not shown). The first telescoping section 188 carries a first spotting element 192 such as a rotary center drill, and the second telescoping section 190 carries a second spotting element 194 such as a rotary center drill. Combined movement of the robot arm 130 and the spotting apparatus 180 permits the first and second spotting elements 192, 194 to be driven to selected locations relative to the condyles of the femur F. The spotting elements 192, 194 may then be used to form identifiable reference features in the femur F, such as small blind center drill holes. These reference features may then be used to provide a fixed position reference on the femur F for further surgical procedures.

The robot arm 130 is suitable for being mounted to different objects. As shown in FIG. 18, it may be mounted to the baseplate 42 of the tensioner-balancer 40. The mount is configured such that the robot arm 130 and the actuating instrument 70 may be simultaneously mounted to the tensioner-balancer 40.

Figure 25:
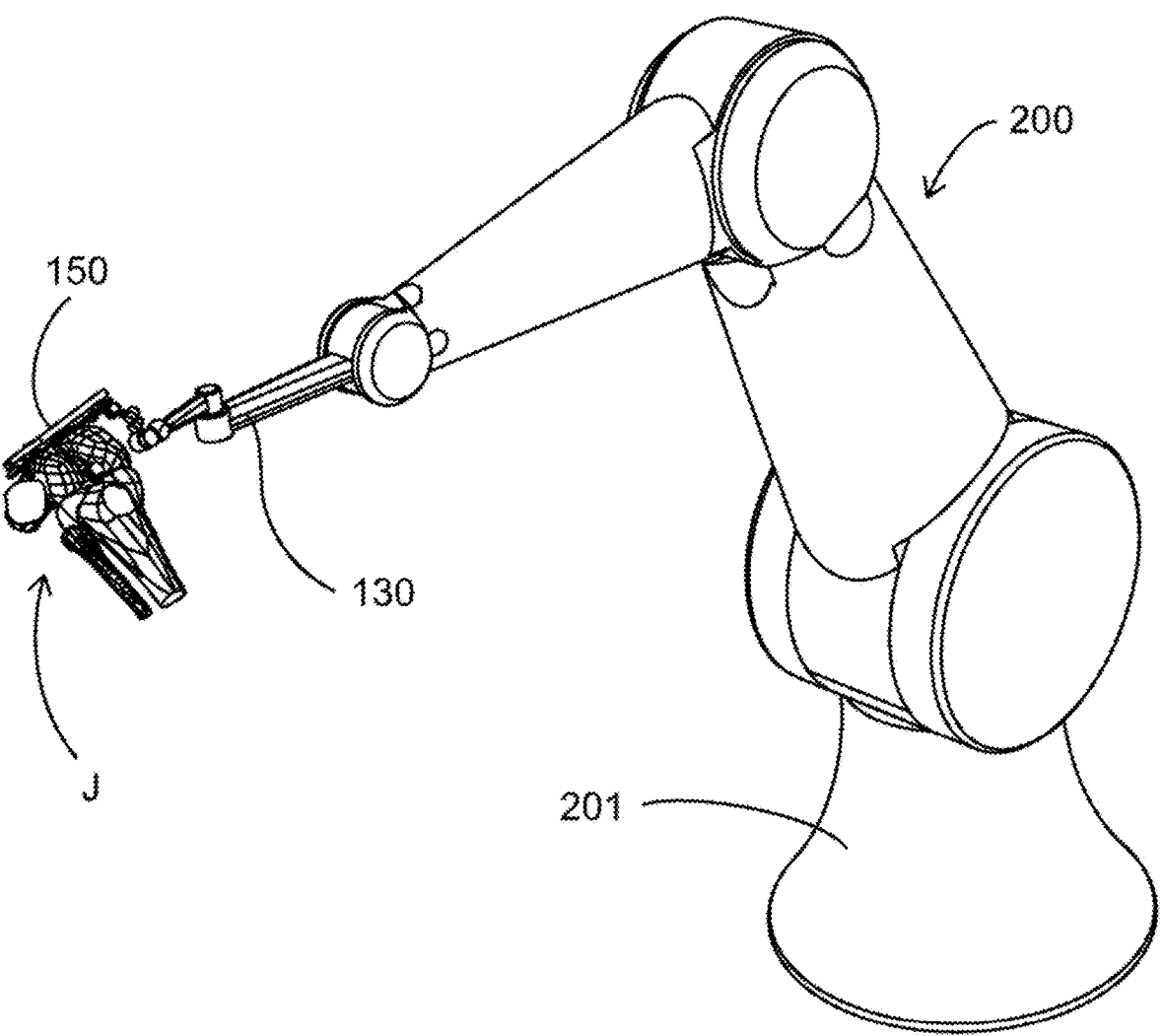
FIG. 25 is a perspective view of a robot arm mounted to a floor-standing robot.
Figure 26:
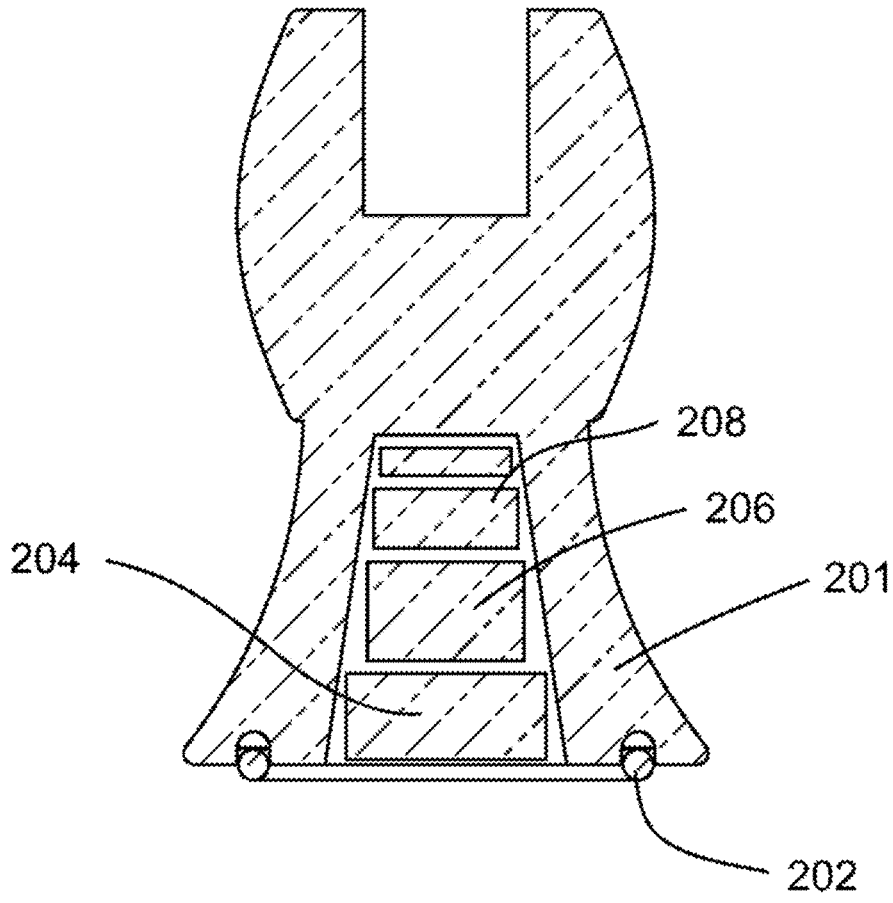
FIG. 26 is a schematic cross-sectional view of a base of the floor-standing robot of FIG. 25.

Alternatively, as shown in FIG. 25, it may be mounted as an end effector to a conventional floor-standing robot 200. The floor-standing robot 200 may be mobile, for example by being mounted on casters (not shown). Alternatively (FIG. 26) its base 201 may include a peripheral skirt 202, blower 204, power source 206, and control electronics 208 enabling it to selectively float or hover on an air cushion so that it can move or be moved over a floor with low friction. The blower 204 may alternatively be used to provide suction in order to fix the floor-standing robot in one position as desired.

The apparatus described above is suitable for various surgical procedures.

In one procedure, the tensioner-balancer 40 is used to evaluate the knee and to model the articular surfaces of the knee over its range of motion.

More particularly, the locus of points of contact of the femur F and the top plate 44 are modeled as a medial spline and a lateral spline.

To carry out this modeling, the tensioner-balancer is inserted between the femur F and the tibia T. As shown in FIG. 14, this is accomplished after having first made the tibial plateau cut. However, the tibial plateau cut is not required.

The actuating instrument 70 is coupled to the tensioner-balancer 40. Femoral tracking marker 88 is implanted to the femur F. At least one of tibial tracking marker 90 and instrument tracking marker 86 is placed.

The tensioner-balancer 40 is extended to apply a load to the knee joint. While different modes of operation are possible, one exemplary mode is to extend the tensioner-balancer 40 until a predetermined distraction load (also referred to as distraction force) is applied. Feedback control or mechanical spring preload may then be used to maintain this distraction load, while the top plate 44 is permitted to pivot freely. One example of a suitable distraction load is approximately 130 N (30 lb.) to 220 N (50 lb.). As one option, the distraction load may be constant over the knee joint range of motion. As another option, the distraction may be a predetermined variable load, where the distraction load is correlated to knee joint position. As another option, the tensioner-balancer may be used to maintain a constant distraction gap while the knee joint is moved through its range of motion.

Figure 27:
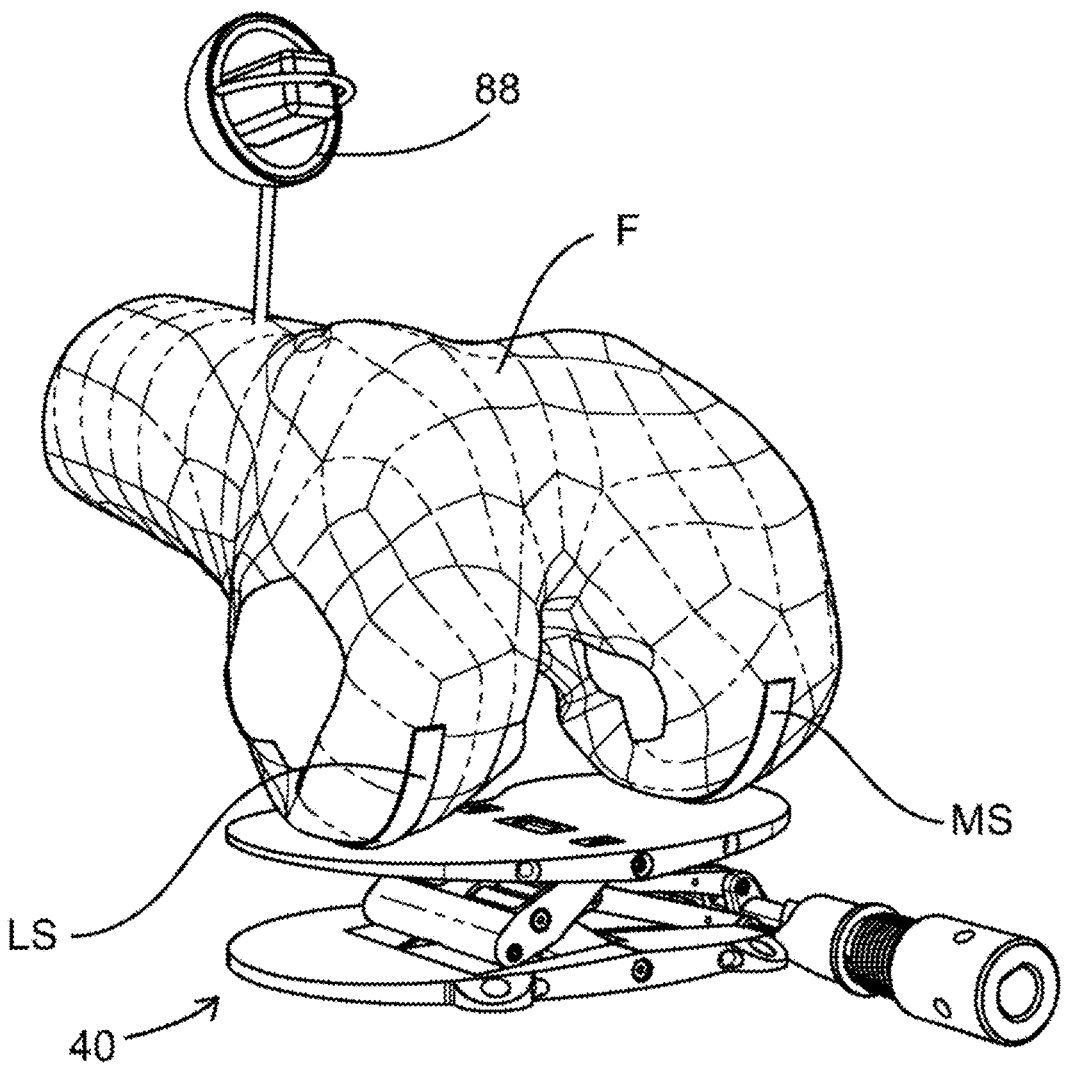
FIG. 27 is a perspective view showing a femur in contact with a tensioner-balancer.
Figure 28:
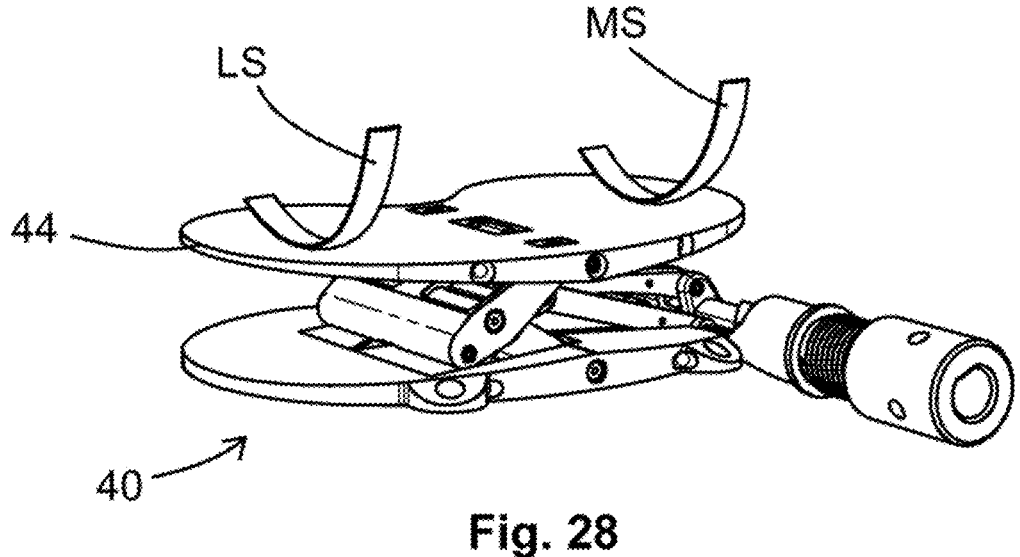
FIG. 28 is a perspective view showing plots of collected spline data superimposed on the top plate of a tensioner-balancer.
Figure 29:
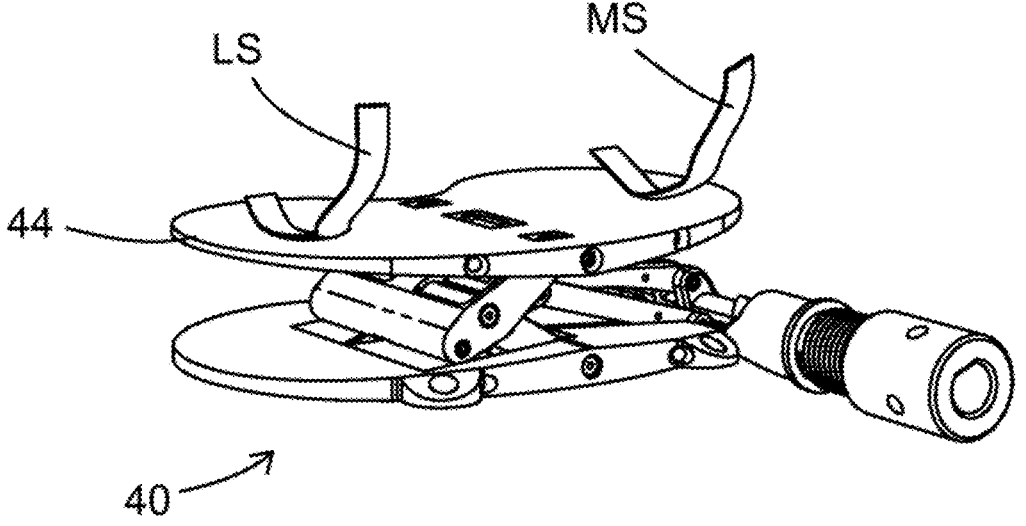
FIG. 29 is another perspective view showing plots of collected spline data superimposed on the top plate of a tensioner-balancer.

The knee joint J is then moved through its range of motion from full extension to full flexion while collecting data from the tensioner-balancer 40 and tracking markers 86, 88, 90. Specifically, the instantaneous location of the load centers LC and MC are recorded and correlated to the flexion angle of the knee joint (as determined from the tracking marker data). The recorded data is represented by the medial spline "MS" and the lateral spline "LS" as shown in FIG. 27. FIGS. 28 and 29 show the splines superimposed on the top plate of the tensioner-balancer 40. FIG. 28 illustrates idealized or nominal shape splines. FIG. 29 illustrates splines indicative of discontinuities or "notching" which may be found in an actual or pathological knee joint J. The splines may be characterized by two or more points (a Starting point and Terminal point, with zero or more Intermediary points in between), each with a location (defined by cartesian or polar coordinates relative to a fixed reference point defined by tracker on the tensioner-balancer baseplate), a direction, and a first and second derivative.

The spline information may be used to select an appropriate endoprosthesis, specifically a femoral component. Multiple femoral components of different sizes and articular surface profiles may be provided, and the one which has the best fit to the splines MS, LS may be selected for implantation. Alternatively, the spline information may be used to generate a profile for manufacture of a patient-specific femoral component.

Figure 40:
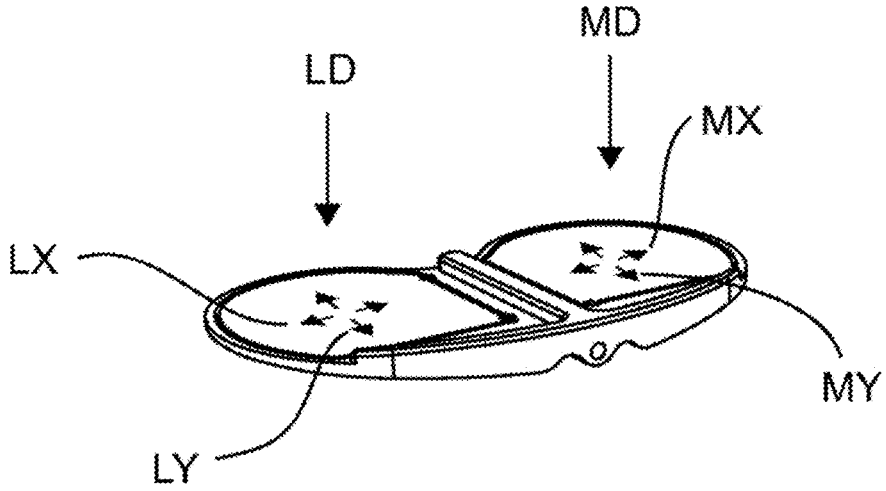
FIG. 40 is a diagram showing a tensioner-balancer labeled with data parameters.
Figure 40:
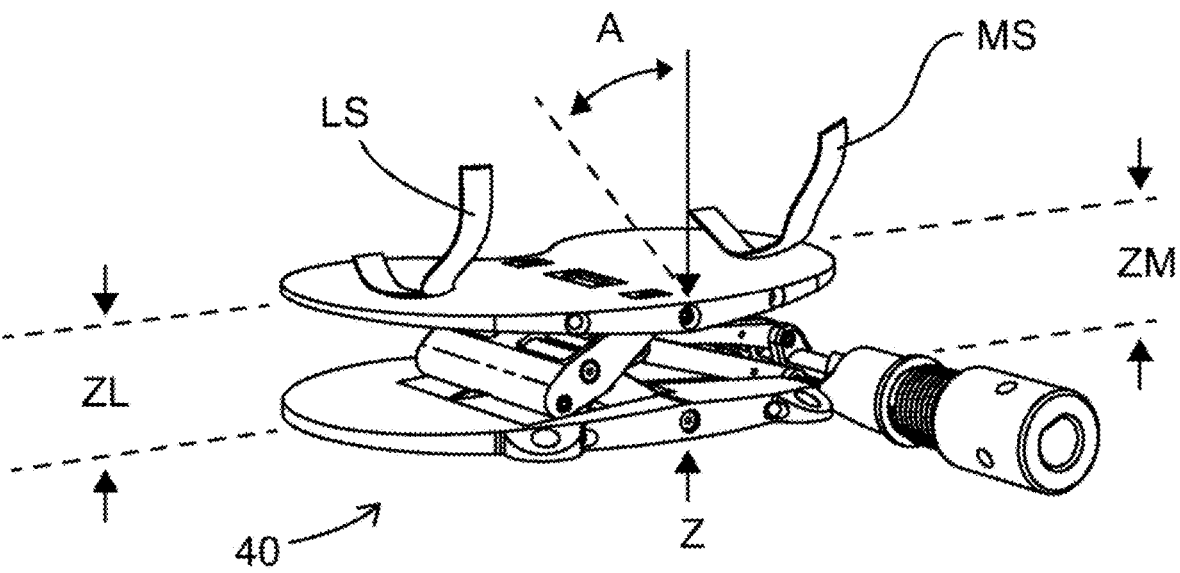
Figure 41:
FIG. 41 is a diagram showing a knee joint and tensioner-balancer labeled with data parameters.

The spline information may be used in conjunction with other information to determine appropriate cutting planes for the femur F. For example, the back surface 28 of the femoral component 14 has a known relationship to the articular surface 30. The desired final location and orientation of the articular surface 30 is known in relation to the top plate 44 of the tensioner-balancer 40, which serves as a proxy for the tibial component 12. The final location of the tibial component 12 is known in relationship to the position of the tibial tracking marker 90. Finally, the actual orientation and location of the femur F in relation to the other parts of the joint J is known from the information from the femoral tracking marker 88. Using appropriate computations, the orientation and location of the cutting planes of the femur F can be calculated and referenced to the position of the tensioner-balancer 40. With reference to FIGS. 40 and 41, it will be understood that the tensioner-balance 40 and associated tracking apparatus may be used to collect the following data related to the knee joint: distraction height "Z" of the top plate 44, tilt angle "A" (i.e., varus-valgus) of the top plate 44), medial and lateral distraction heights "ZM", "ZL" (e.g., derived from the top plate distraction height and top plate tilt angle), the medial and lateral spline data, the position of the contact points of the femur F on the top plate (medial-lateral and anterior-posterior) (MX, MY, LX, LY), the distraction load on the medial and lateral condyles (MD, LD), the knee joint flexion angle "FA", and the abovementioned 6-DoF position data for each tracking marker (X, Y, Z position and Xr, Yr, Zr rotation).

Figure 30:
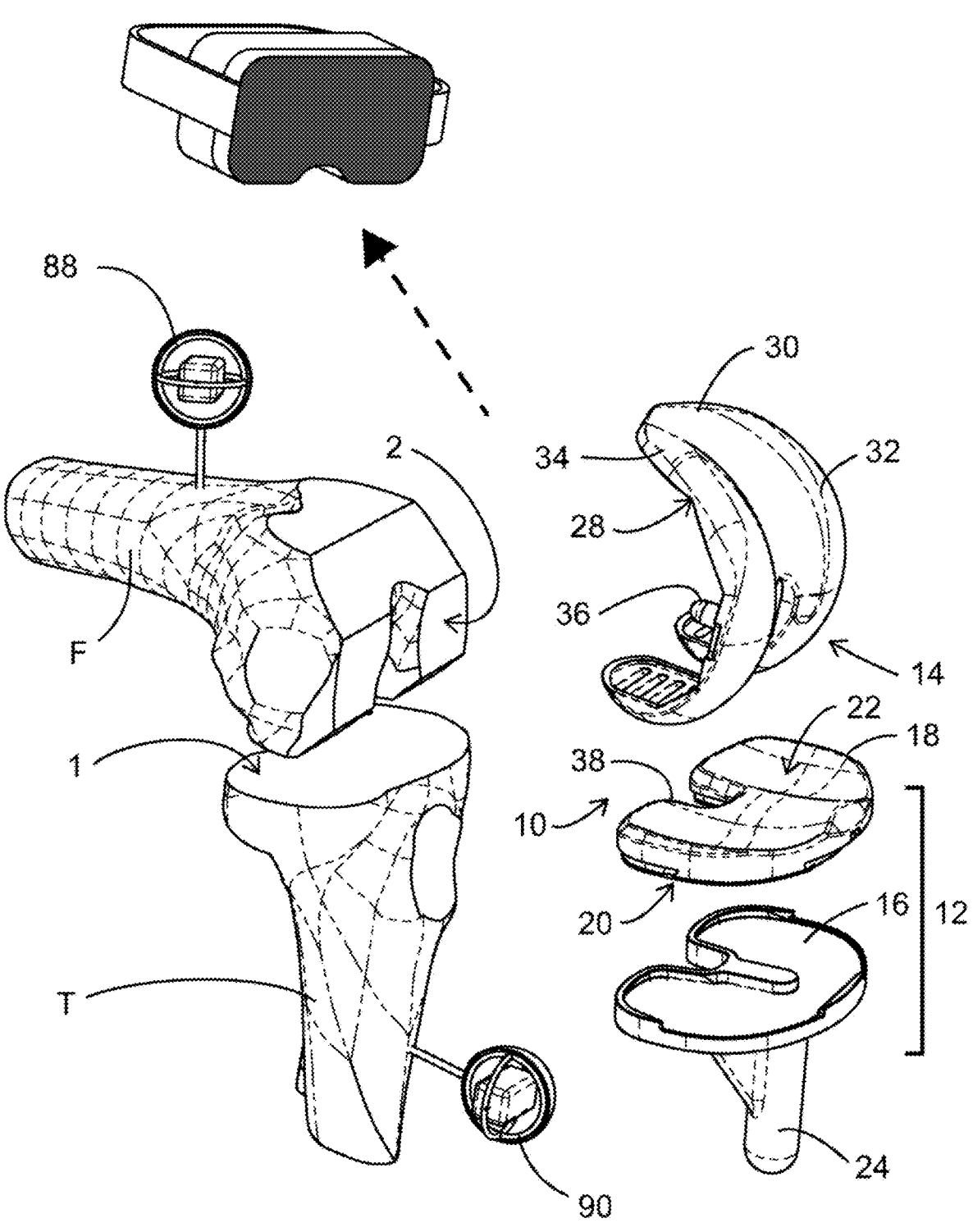
FIG. 30 is a perspective view of a human knee joint in conjunction with an exploded view of an endoprosthesis.

A nominal distal femoral cutting plane 2 (FIG. 30) may be determined by anatomical analysis using known anatomical references and techniques. For example, this plane 2 could be uniformly spaced away from and parallel to the tibial cutting plane 1 (i.e., a nominal cut). Alternatively, this plane 2 could be at an oblique angle to the tibial cutting plane 1, in one or more planes (i.e., simple or compound tilted cut, potentially usable as a corrective cut).

In one method, the cable saw 150 may be coupled to the robot arm 130 which is in turn mounted to the tensioner-balancer as seen in FIG. 16. The cutting plane information may then be used to drive the robot arm 130 with attached cable saw 150 to make the cuts in the femur F.

In another method, the cable saw 150 may be coupled to the robot arm 130 which is in turn mounted to the floor-standing robot 201 as seen in FIG. 25. The cutting plane information may then be used to drive robot arm 130 with attached cable saw 150 to make the cuts in the femur F.

Figure 31:
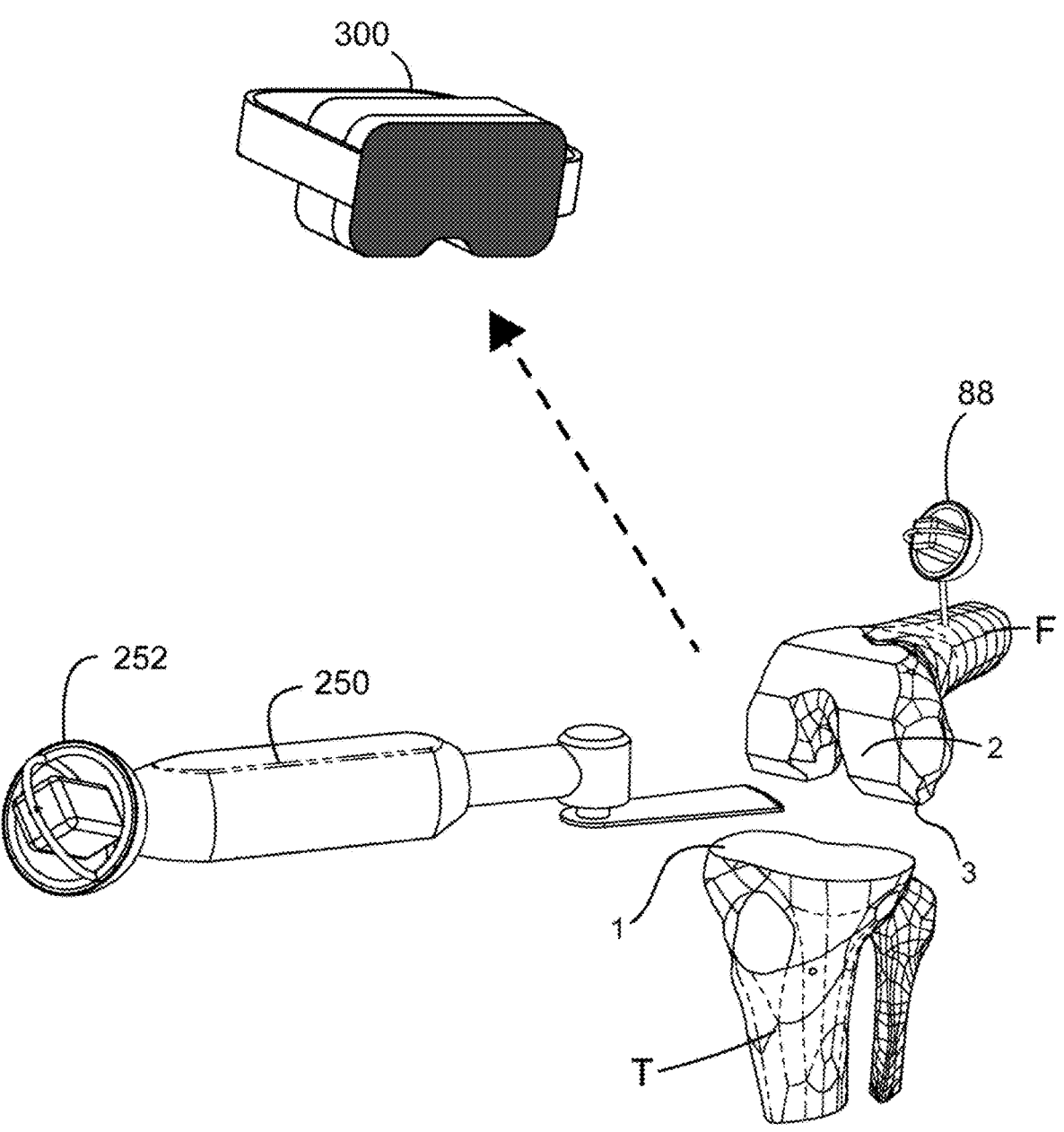
FIG. 31 is a perspective view of a human knee joint in conjunction with a mixed reality display device and an instrumented bone saw.

Information from the tensioner-balancer 40 and tracking markers may be used with hand-held equipment. Once the cutting planes are determined, the tracking markers 86, 88, or 90 may be used to guide a bone saw 250 equipped with a tracking marker 252 to make the distal femoral cut 2 at appropriate angle and location, as depicted in FIG. 31. In this context, the cutting plane (or a portion thereof) defines a computed tool path. This guidance is possible because intercommunication between the bone saw 250 and the associated tracking marker 252 will give the relative position and orientation of the bone saw 250 to that tracking marker. The cutting guidance may be provided in the form of information displayed on the remote display 84 described above. For this purpose, 2-way data communications may be provided between and among the bone saw 250 (or other surgical instrument), the tracking markers 86, 88, or 90, and the remote display 84.

It should be noted that the bone saw 252 can be guided with reference to only a single tracking marker 88 coupled to the femur F. Alternatively, the cutting guidance (optionally along with other information, such as the virtual future position of the drilled holes and implants used) may be displayed on a body-worn display providing 2D or 3D graphics or providing a holographic heads-up display with an information panel (e.g., a Virtual Reality or augmented reality or mixed reality headset 300). Alternatively, the cutting guidance may be provided to a conventional robot 301 (FIG. 32) to which the bone saw is mounted.

Figure 32:
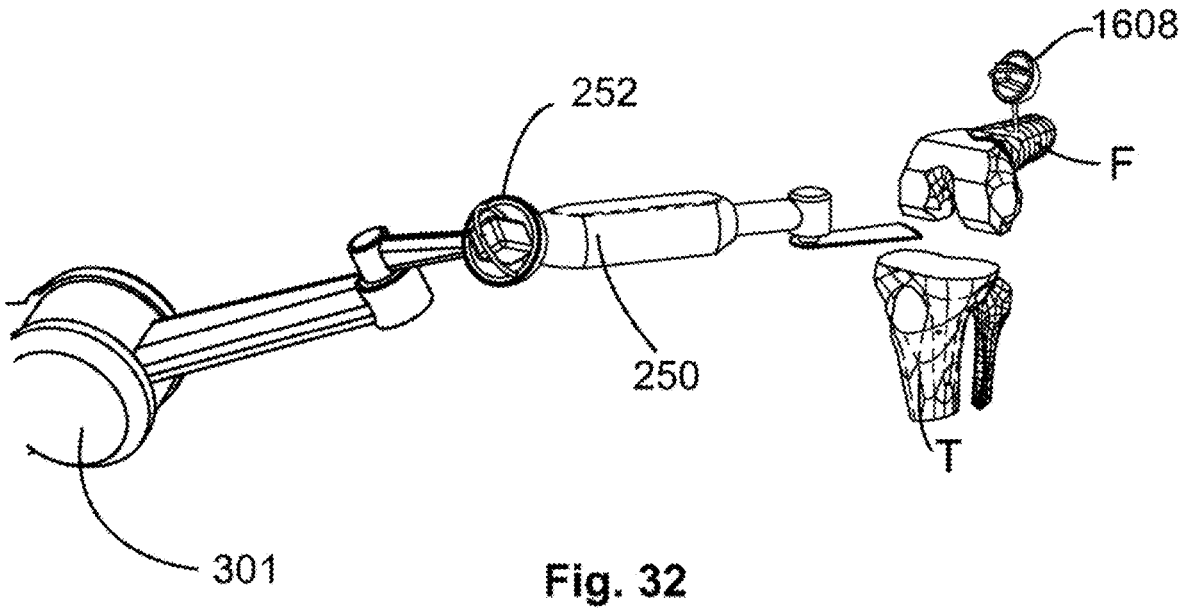
FIG. 32 is a perspective view of a human knee joint in conjunction with an instrumented bone saw coupled to a robot.
Figure 33:
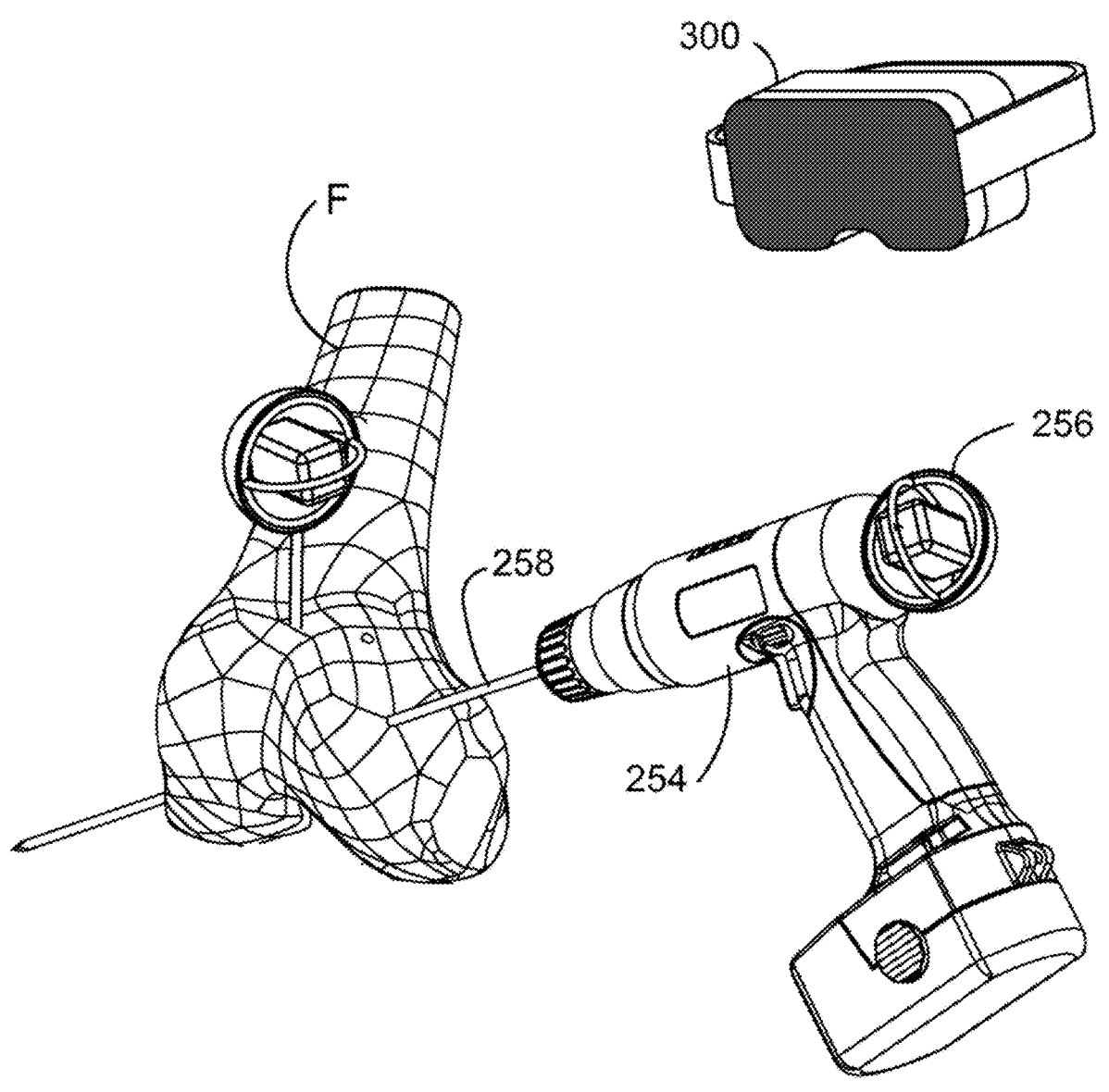
FIG. 33 is a perspective view of a human knee joint in conjunction with a mixed reality display device and an instrumented drill.
Figure 34:
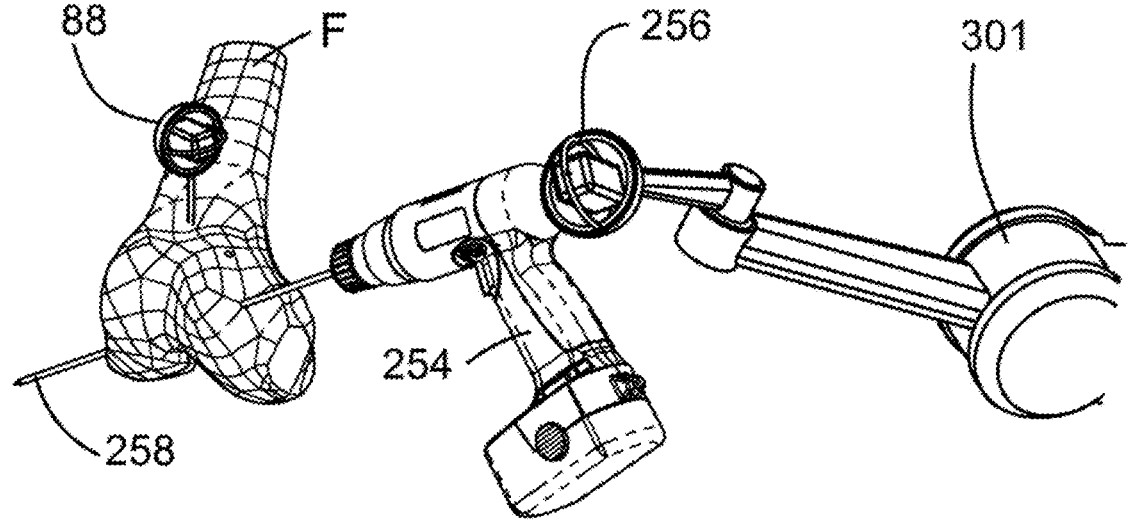
FIG. 34 is a perspective view of a human knee joint in conjunction with an instrumented drill coupled to a robot.

Information from the tensioner-balancer 40 and tracking markers may optionally be used for drilling holes, for example to anchor tensile elements. Referring to FIG. 32, once a position of a hole to be drilled is determined, the tracking markers 86, 88, or 90 may be used to guide a cordless drill 254 equipped with a tracking marker 256 to drill a hole, with the drill bit 258 extending an appropriate angle. In this context, the hole to be drilled (or a portion thereof) defines a computed tool path. Guidance along the tool path is possible because intercommunication between the cordless drill 254 and the tracking marker 256 will give the relative position and orientation of the cordless drill 254 to those markers. The drilling guidance may be provided in the form of information displayed on the remote display 84 described above. For this purpose, two-way data communications may be provided between and among the cordless drill 254 (or other surgical instrument), the tracking markers 86, 88, or 90, the actuating instrument 70, and the remote display 84. It should be noted that the drill 254 can be guided with reference to only a single tracking marker 88 coupled to the femur F. Alternatively, the drilling guidance (optionally along with other information, such as the virtual future position of the drilled holes and implants used) may be displayed on a body-worn display providing 2D or 3D graphics or providing a holographic heads-up display with an information panel (e.g., a Virtual Reality or augmented reality or mixed reality headset 300). Alternatively, the drilling guidance may be provided to a conventional robot 301 (FIG. 34) to which the bone saw is mounted.

Figure 35:
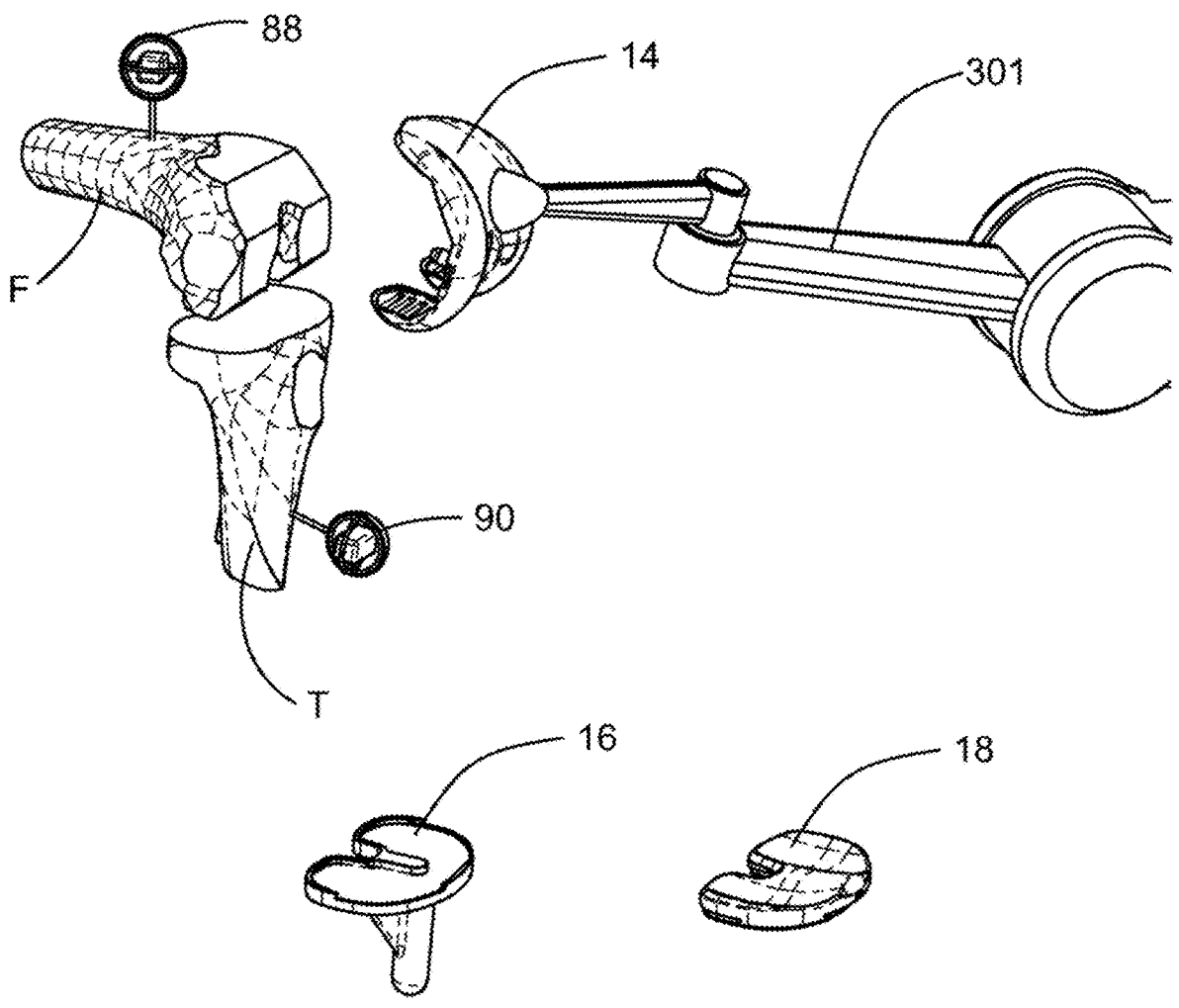
FIG. 35 is a perspective view of a human knee joint in conjunction with an a robot that is manipulating an endoprosthesis.

Information from the tensioner-balancer 40 and tracking markers may optionally be used for automated placement of components. Referring to FIG. 35, the tracking markers 86, 88, or 90 may be used to guide a robot 301 to implant one or more of the endoprosthetic components into the knee joint J, such as the tibial tray 16, insert 18, and/or femoral component 14 to which the bone saw is mounted.

Figure 36:
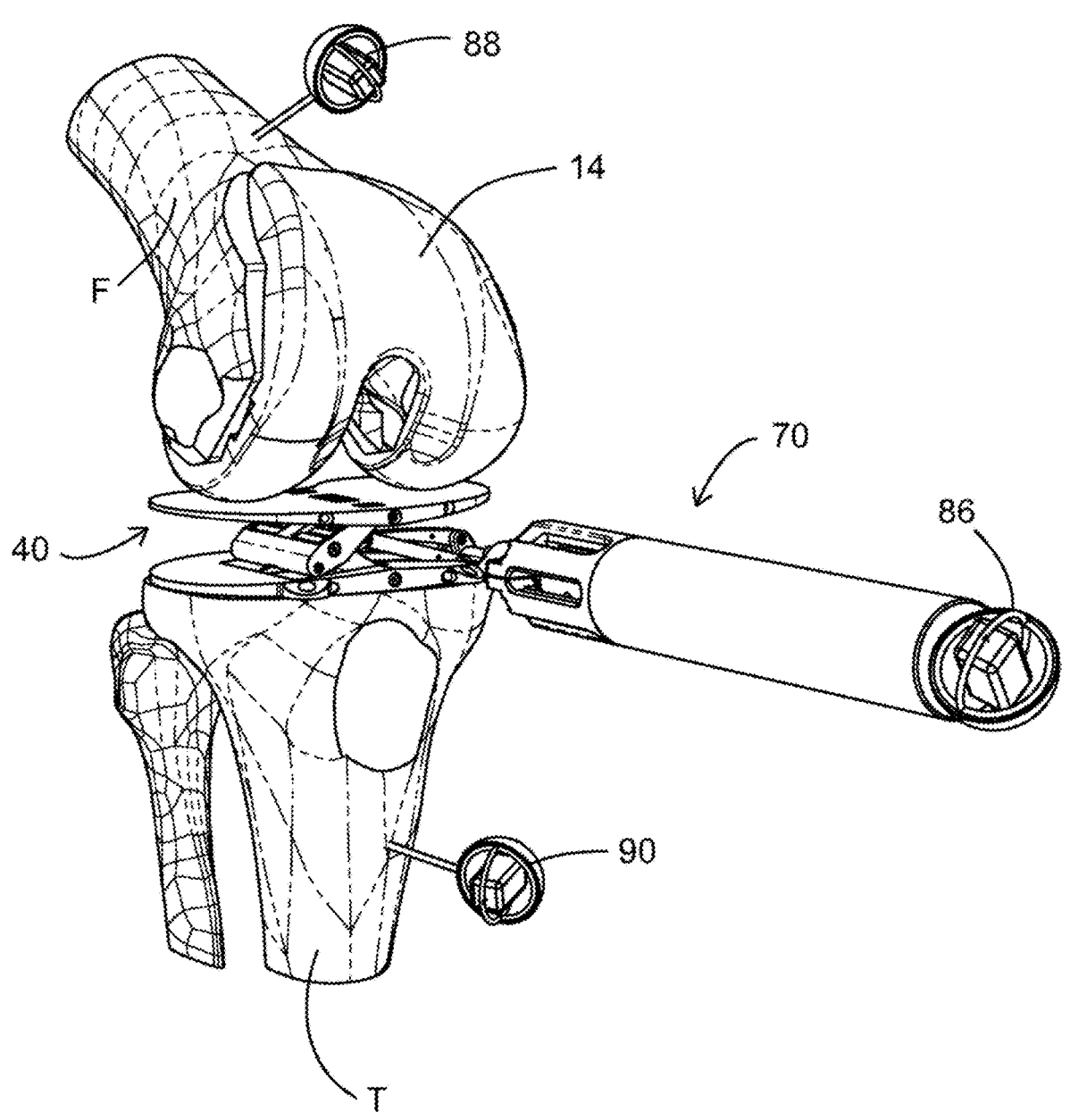
FIG. 36 is a perspective view of a human knee joint having a trial endoprosthetic device implanted, in conjunction with a tensioner-balancer.

As seen in FIG. 36, the tensioner-balancer 40 may be used with a trial implant (femoral component 14) to collect data and evaluate the femoral component 14.

In addition to retaining the patients' PCL in a knee arthroplasty, it may be augmented (reinforced) using one or more artificial tensile members. The term "tensile member" as used herein generally refers to any flexible element capable of transmitting a tensile force. Nonlimiting examples of known types of tensile members include sutures and orthopedic cables. Commercially-available tensile members intended to be implanted in the human body may have a diameter ranging from tens of microns in diameter to multiple millimeters in diameter. Commercially-available tensile members may be made from a variety of materials such as polymers or metal alloys. Nonlimiting examples of suitable materials include absorbable polymers, nylon, ultra-high molecular weight polyethylene ("UHMWPE") or polypropylene titanium alloys, or stainless steel alloys. Known physical configurations of tensile members include mono-filament, braided, twisted, woven, and wrapped. Optionally, the tensile member may be made from a shape memory material, such as a temperature-responsive or moisture-response material.

Figures 37, 38:
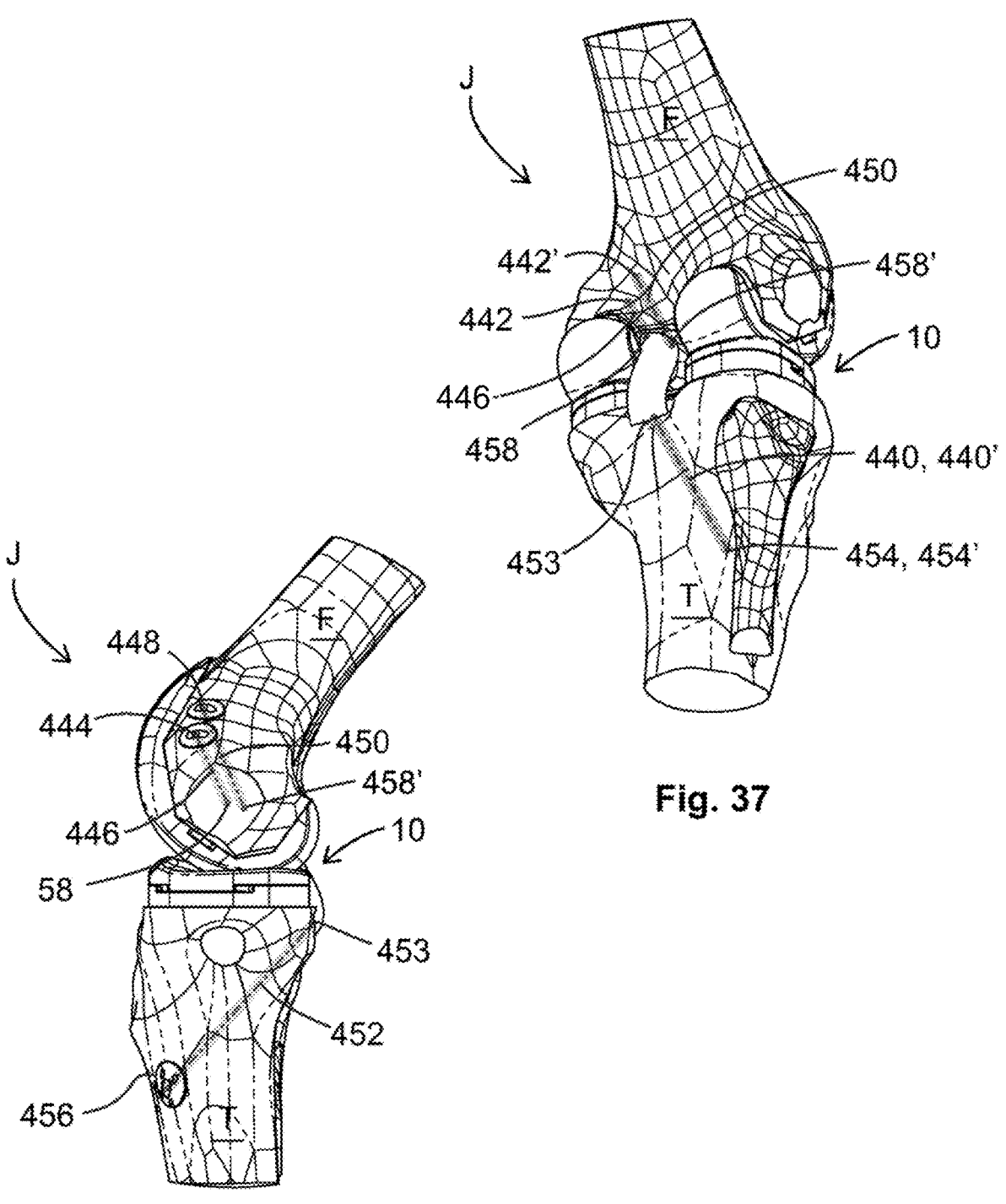
FIG. 37 is a perspective view of a posterior aspect of a human knee joint having a posterior cruciate ligament reinforced by artificial tensile member.
FIG. 38 is a view of the medial aspect of the human knee joint of FIG. 37.

FIGS. 37 and 38 illustrate a tensile member passing through transosseous passaged formed in bone (e.g., by drilling), fixed by anchors, and routed across the posterior aspect of a human knee joint J. The tensile member replaces or augments or reinforces or tethers the PCL.

In the illustrated example, two tensile members are present, referred to as first and second tensile members 440, 440' respectively.

The first tensile member 440 has a first end 442 secured to the femur F on the outboard side thereof, by a first anchor 444. (With reference to this example, the terms "inboard" and "outboard" are used to describe locations relative to their distance from the meeting articular surfaces of the joint J. For example, the endoprosthesis 10 would be considered "inboard" of the joint J, while the anchor 444 would be considered "outboard"). The first tensile member 440 passes through a first femoral passage 446 formed in the femur F, exiting the inboard side of the femur F.

The second tensile member 440' has a first end 442' secured to the femur F on the outboard side thereof, by a second anchor 448. The second tensile member 440' passes through a second femoral passage 450 formed in the femur F, exiting the inboard side of the femur F.

The first and second tensile members 440, 440' span the gap between femur F and tibia T and enter a tibial passage 452 at an inboard side. The first and second tensile members 440, 440' pass through the tibial passage 452 at a single entry 453, exiting the outboard side of the tibia T. Second ends 454, 454' of the first and second tensile members 440, 442' are secured with a third anchor 456.

The term "anchor" as it relates to elements 444, 448, and 456 refers to any device which is effective to secure a tensile member passing therethrough. Nonlimiting examples of anchors include washers, buttons, flip-anchors, adjustable loop devices, fixed loop devices, interference screw devices, screw plates, ferrules, swages, or crimp anchors.

The tensile members 440, 440' can be routed through or along the PCL.

Figure 39:
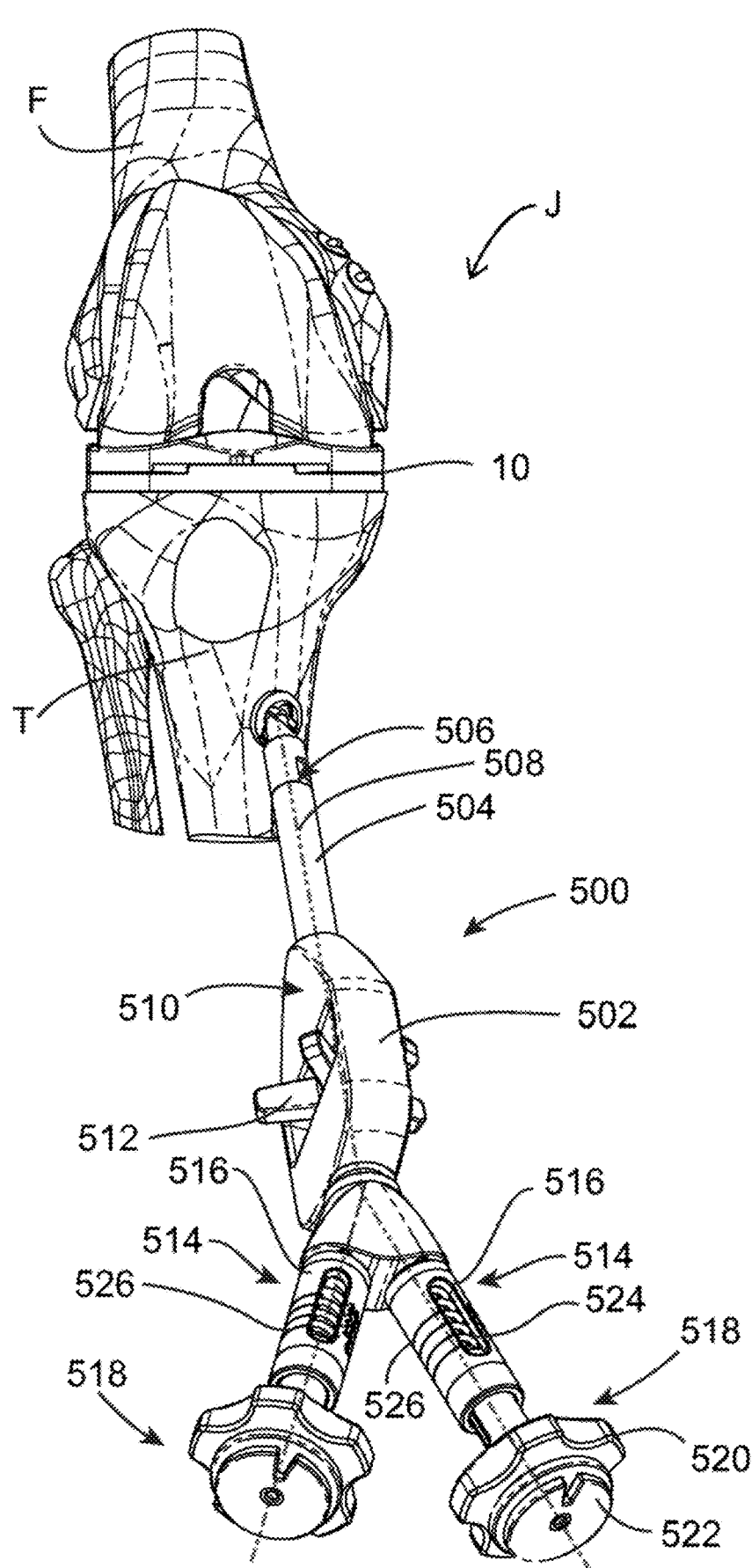
FIG. 39 is a view of the anterior aspect of the human knee joint in combination with an instrument for tensioning an artificial tensile member.

FIG. 39 illustrates an exemplary insertion instrument 500 which may be used to insert, tension, and activate swage-type anchors. The basic components of the insertion instrument 500 are a body 502, a stem 504 extending from the body 502 and having an anchor connection mechanism 506 disposed at a distal end thereof, a hollow pushrod 508 extending through the stem 504 and slidably movable between retracted and extended positions, and a driving mechanism 510 for moving the pushrod 508 between retracted and extended positions. The stem 504 and the pushrod 508 may be rigid or flexible.

In the illustrated example, the driving mechanism 510 comprises an internal threaded mechanism which is manually operated by a star wheel 512.

A tensioner 514 is part of or connected to the insertion instrument 500. It has a housing 516. A shuttle assembly 518 including an adjustment knob 520 and a grooved spool 522 is received inside the housing 516. A compression spring 524 is captured between the shuttle assembly 518 and the housing 516. The shuttle assembly 518 can translate forward and aft relative to the housing 516 in response to rotation of the adjustment knob 520.

In use, a first end of a tensile member 440 passes through the hollow interior of tensioner 514 and is secured to the spool 522. The tension applied to the tensile member 440 may be indicated, for example, by observing the position of the shuttle assembly 518 relative to a calibrated scale 526 on the housing 516. When a suitable final tension is achieved, the star wheel 512 may be operated to actuate the pushrod 508, swaging the tensile member 440 and fracturing the breakaway structure of the anchor. In the illustrated example, two separate tensioners 514 are provided, allowing the tension of each of the tensile members to be set independently.

In one example procedure where two tensile members are used, a first provisional tension is applied to the first tensile member and a second provisional tension is applied to the second tensile member. The second tensile member may have the same or different tension at the first tensile member. Next, the provisional tensions evaluated to determined if they are suitable. In response to the evaluation, they may be increased or decreased. Finally, the anchor may be swaged to secure the tensile members and finalize the tension. In one example, the tension may be from about 0 N (0 lb.) to about 220 N (50 lb.)

The apparatus and method described herein will permit knee arthroplasty with improved patient outcomes with a minimum amount of added equipment and procedures.

The apparatus and techniques described herein are also applicable to surgical procedures and arthroplasty on other joints. The apparatus can be used to distract, track, and proceed with corrective actions based on distraction feedback. For example, these techniques may be used on hip or shoulder joints.

The foregoing has described apparatus and methods for knee arthroplasty. All of the features disclosed in this specification, and/or all of the steps of any method or process so disclosed, may be combined in any combination, except combinations where at least some of such features and/or steps are mutually exclusive.

Each feature disclosed in this specification may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends, or to any novel one, or any novel combination, of the steps of any method or process so disclosed.

What is claimed is:

1. A method of evaluating a human knee joint which includes a femur bone, a tibia bone, and ligaments, wherein the ligaments are under anatomical tension to connect the femur and tibia together, creating a load-bearing articulating joint, the method comprising:

inserting into the knee joint a tensioner-balancer that includes a femoral interface surface, and at least one force sensor;

providing an electronic receiving device;

moving the knee joint through at least a portion of its range of motion;

while moving the knee joint, using the electronic receiving device to collect data from the at least one force sensor;

processing the collected force data to produce a digital geometric model of the knee joint, wherein the digital geometric model includes:

a medial spline representing a locus of points of contact of a medial condyle of the femur with the femoral interface surface, over a range of knee flexion angles, each of the points of contact characterized by a location, a direction, and a first and second derivative; and a lateral spline representing a locus of points of contact of the femur with the femoral interface surface over a range of knee flexion angles, each of the points of contact characterized by a location, a direction, and a first and second derivative; and storing the digital geometric model for further use.

2. The method of claim 1, wherein the femoral interface surface is defined by a top plate, the top plate including a lateral cantilevered pad and a medial cantilevered pad, wherein each cantilevered pad is provided with two or more spaced-apart strain gages at the intersection between the respective cantilevered pad and a stationary portion of the top plate.

3. The method of claim 1 further comprising:

connecting at least one tracking marker to the knee joint;

collecting position data from the tracking marker while moving the knee joint; and, using the position data and the force data to produce the geometric model.

4. The method of claim 1 further comprising:

computing one or more tool paths passing through the knee joint;

coupling at least one tracking marker to the knee joint;

receiving data representing an actual position and orientation of a tool relative to the at least one tracking marker;

moving a tool along the one or more tool paths, with reference to the data, so as to remove bone from the knee joint, thereby forming a machined feature in the knee joint.

5. The method of claim 1 wherein the patella remains in its native anatomical position during all steps of the method.

6. The method of claim 1 further comprising using the tensioner-balancer to distract the knee joint.

7. The method of claim 6 wherein the distraction is carried out by:

inserting the tensioner-balancer between the tibia and the femur, with the tensioner-balancer in a retracted position; and moving the tensioner-balancer towards an extended position, so as to urge the tibia and the femur apart and apply tension to ligaments of the knee joint.

8. The method of claim 6 wherein the tensioner-balancer applies a substantially constant force while permitting variable deflection.

9. The method of claim 6 wherein the tensioner-balancer applies a predetermined variable force as the data is collected while moving the knee joint, where the predetermined variable force is correlated to knee joint position.

10. The method of claim 6 wherein the tensioner-balancer maintains a predetermined distraction gap as the data is collected while moving the knee joint.

* * * * *